United States Patent
Sugi et al.

(10) Patent No.: US 6,699,508 B1
(45) Date of Patent: Mar. 2, 2004

(54) SUSTAINED RELEASE ORAL PREPARATIONS OF FASUDIL HYDROCHLORIDE

(75) Inventors: Tomokazu Sugi, Shizuoka-ken (JP); Fumihide Nishio, Mishima (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 09/701,833

(22) PCT Filed: Aug. 4, 1999

(86) PCT No.: PCT/JP99/04196

§ 371 (c)(1),
(2), (4) Date: Dec. 5, 2000

(87) PCT Pub. No.: WO00/09133

PCT Pub. Date: Feb. 24, 2000

(30) Foreign Application Priority Data

Aug. 10, 1998 (JP) .......................................... 10/236606

(51) Int. Cl.⁷ .......................... A61K 9/14; A61K 9/20; A61K 9/22; A61K 9/44; A61K 9/16
(52) U.S. Cl. ...................... 424/497; 424/464; 424/465; 424/468; 424/472; 424/474; 424/475; 424/480; 424/489; 424/491; 424/497
(58) Field of Search .................. 424/464, 465, 424/468, 472, 474, 475, 480, 489, 491, 497

(56) References Cited

U.S. PATENT DOCUMENTS

| | | | |
|---|---|---|---|
| 4,678,783 A | 7/1987 | Hidaka et al. | |
| 4,963,365 A | 10/1990 | Samejima et al. | |
| 4,968,505 A | 11/1990 | Okada et al. | |
| 5,747,507 A | 5/1998 | Ikegaki et al. | |
| 5,942,505 A | 8/1999 | Kawakubo et al. | |
| 5,980,882 A | * 11/1999 | Eichman ................... 424/78.12 |
| 6,153,608 A | * 11/2000 | Hidaka et al. .............. 514/218 |
| 6,271,224 B1 | * 8/2001 | Kapin et al. ................ 514/218 |

FOREIGN PATENT DOCUMENTS

| | | | |
|---|---|---|---|
| EP | 0508653 A1 | 10/1992 | |
| EP | 508653 A1 | * 10/1992 | |
| JP | 2256617 | 10/1990 | |

OTHER PUBLICATIONS

Ishida et al. "Encapsulation of an antivasospastic drug, fasudil, into liposomes, and in vitro stability of the fasudil-loaded liposomes", Int J Pharm. Jan. 31, 2002; 232(1–2):59–67.*

* cited by examiner

Primary Examiner—Thurman K. Page
Assistant Examiner—S. Tran
(74) Attorney, Agent, or Firm—Young & Thompson

(57) ABSTRACT

An oral sustained-release preparation which contains at least one active ingredient selected from the group consisting of fasudil hydrochloride and a hydrate thereof is disclosed. A method for evaluating an oral sustained-release preparation containing the active ingredient, wherein the evaluation is conducted with respect to the sustained-release ability of the active ingredient is also disclosed.

11 Claims, 7 Drawing Sheets

SUSTAINED RELEASE ORAL PREPARATIONS OF FASUDIL HYDROCHLORIDE

BACKGROUND OF THE INVENTION

1. Field of the Invention

The present invention relates to an oral sustained-release preparation. More particularly, the present invention is concerned with an oral sustained-release preparation which contains at least one active ingredient selected from the group consisting of fasudil hydrochloride and a hydrate thereof, the preparation comprising at least one sustained-release coated particle comprising a core having a surface and a coating formed on the surface of the core, wherein the core contains the active ingredient and the coating comprises a coating base material and a specific insoluble auxiliary material, the preparation exhibiting a specific dissolution rate with respect to the active ingredient, as measured by the dissolution test. The present invention is also concerned with a method for evaluating an oral sustained-release preparation containing the active ingredient, the evaluation being conducted with respect to the sustained-release ability of the active ingredient.

By using the oral sustained-release preparation of the present invention, it becomes possible to surely control the release of fasudil hydrochloride from the preparation, so that a desired amount of fasudil hydrochloride is continued to be released from the preparation for a long period of time, and that the effect of fasudil hydrochloride is maintained for a relatively long period of time. Therefore, the frequency of the administration of the preparation becomes low, so that the burden of the patient who has to take the preparation can be decreased and the compliance with respect to the administration of the preparation can be improved. As a result, the therapeutic effect of fasudil hydrochloride is rendered reliable. Therefore, the oral sustained-release preparation of the present invention is extremely useful.

2. Prior Art 1-(5-Isoquinolinesulfonyl)homopiperazine hydrochloride (hereinbelow referred to as "fasudil hydrochloride") has excellent vasodilative activity and is clinically used for treating cerebral vasospasm (which is likely to occur after the operation of a patient suffering from subarachnoid hemorrhage), cerebral ischemic symptoms accompanying the cerebral vasospasm, and the like, wherein the above-mentioned fasudil hydrochloride is used in the form of a parenteral preparation which is available under tradename "Eril Inj." (registered trademark for the product produced and sold by Asahi Kasei Kogyo Kabushiki Kaisha, Japan) (see Unexamined Japanese Patent Application Laid-Open Specification No. 5-3851 (corresponding to U.S. Pat. No. 4,678,783)).

There are two conventionally known different types of crystals of fasudil hydrochloride, i.e., crystals containing no water of crystallization (hereinbelow referred to as "fasudil hydrochloride anhydride") and crystals containing water of crystallization (hereinbelow referred to as "fasudil hydrochloride hydrate") (see International Patent Application Publication No. WO97/02260 (corresponding to EP 0 870 767 A1)).

SUMMARY OF THE INVENTION

Fasudil hydrochloride has excellent vasodilative activity. For this reason, it is expected that fasudil hydrochloride is provided in the form of various types of preparations, wherein the administration route, manner of administration, dosage and the like of the preparations are different from those of the above-mentioned parenteral preparation.

For example, due to the excellent vasodilative activity, fasudil hydrochloride can be used as a drug for treating an ischemic disease (especially, angina pectoris). With respect to a preparation containing fasudil hydrochloride as an active ingredient, which is used as a drug for treating an ischemic disease, an oral preparation can be taken by the patient himself at his home, whereas a parenteral preparation must be administered by a doctor at a hospital. Therefore, the oral preparation can extremely decrease the burden of the patient suffering from an ischemic disease, which needs his attendance at a hospital for the treatment of the disease.

From the above-mentioned viewpoint, the present inventors attempted developing an oral preparation containing fasudil hydrochloride as an active ingredient, which is used as a drug for treating an ischemic disease (such as angina pectoris).

In the course of the development of the oral preparation, it has been found that the conventional oral preparation (containing fasudil hydrochloride as an active ingredient) is required to be administered as frequently as 3 times a day for achieving a satisfactory therapeutic effect. However, with respect to a disease (such as an ischemic disease) which should be treated by administering a drug for a long period of time, when a preparation used as a drug for treating the disease should be frequently administered, in many cases, the so-called "compliance" with respect to the administration of the preparation is low. This low compliance is caused by the fact that when the preparation should be frequently administered, in many cases, the patient forgets to take the preparation. As a result, the therapeutic effect of the preparation cannot be surely achieved.

For this reason, in order to surely achieve the therapeutic effect of the preparation, it is considered preferable that the frequency of the administration of the preparation is lowered so that the compliance is improved and the burden of the patient who has to take the preparation is decreased.

As an example of the method effective for lowering the frequency of the administration of the preparation, there can be mentioned a method in which the preparation is prepared in a sustained-release form. Therefore, the present inventors attempted developing a sustained-release preparation containing fasudil hydrochloride as an active ingredient. As a result, it has been found that in order to develop such a preparation, the below-mentioned two problems should be solved.

One of the two problems is how to realize a controlled dissolution of fasudil hydrochloride.

Generally, when the dissolution rate of the drug from the preparation is appropriately controlled, the drug is gradually released from the preparation (which contains a relatively large amount of the drug) over a relatively long period of time (hereinafter referred to simply as "over a long period of time"). When such a preparation (sustained-release preparation) is administered to a patient, a desired amount of the drug is gradually released from the preparation over a long period of time. As a result, the concentration of the drug in the blood of the patient is kept in a desired range, so that the effect of the drug is maintained for a long period of time. Further, by virtue of the effect maintained for a long period of time, the frequency of the administration of the preparation can be lowered.

There are many reports on the techniques for producing a sustained-release preparation. These techniques have been applied to many drugs, and various kinds of useful sustained-release preparations have been developed.

However, it is extremely difficult to control, by conventional methods, the release of fasudil hydrochloride from the preparation containing fasudil hydrochloride. In fact, the present inventors tried to develop a sustained-release preparation containing fasudil hydrochloride as an active ingredient using various techniques reported up to the present, but fasudil hydrochloride was rapidly released from the preparation, and it was not possible to control the release of fasudil hydrochloride. This problem is essentially caused by the fact that fasudil hydrochloride is extremely soluble in water.

In addition, in order to maintain the effect of fasudil hydrochloride for a long period of time, the concentration of the active metabolite of fasudil hydrochloride (mentioned below) in blood should be kept in a desired range for a long period of time. In order to achieve this, it is required to use a preparation in which even in the upper portion of the digestive tract (in which the amount of the internal liquid of the digestive tract is large), fasudil hydrochloride is not rapidly released from the preparation, and in which even in the lower portion of the digestive tract (in which the amount of the internal liquid in the digestive tract is small), the amount of fasudil hydrochloride released from the preparation is satisfactory.

For this reason, a sustained-release preparation containing fasudil hydrochloride as an active ingredient should exhibit the following two contradictory functions:

i) surely preventing rapid release of fasudil hydrochloride, even in the presence of a large amount of water, and ii) surely releasing fasudil hydrochloride in a satisfactory amount for a long period of time, even in the presence of a small amount of water.

By a conventional method, it was extremely difficult to develop such a preparation.

The remainder of the two problems is how to control the kinetics of fasudil hydrochloride in a living body.

Most of fasudil hydrochloride (which is orally administered to a human) is metabolized and transferred to circulating blood. Only a small amount of fasudil hydrochloride is transferred to circulating blood without being metabolized. The main metabolite generated from fasudil hydrochloride is 1-hydroxy derivative (in which a hydroxyl group is introduced into the 1-position of the isoquinoline skeleton of fasudil hydrochloride), and this 1-hydroxy derivative exhibits pharmaceutical activities in a living body. In other words, actually, the pharmaceutical activities of fasudil hydrochloride are exhibited by this 1-hydroxy derivative (hereinafter, this 1-hydroxy derivative, which is an active metabolite derived from fasudil hydrochloride, is referred to simply as the "active metabolite"). Therefore, in order to maintain the pharmaceutical activities of fasudil hydrochloride for a long period of time, the concentration of this active metabolite (not fasudil hydrochloride as such) in the blood should be kept in a desired range for a long period of time.

However, the active metabolite is rapidly eliminated from blood. Therefore, in order to keep the concentration of the active metabolite in the blood in a desired range for a long period of time, the active metabolite should be continued to be transferred to circulating blood. In order to achieve this, it is considered to be required that, during the transfer of the preparation containing fasudil hydrochloride as an active ingredient (which is orally administered) to the lower portion of the digestive tract through the entrance into the digestive tract, a desired amount of fasudil hydrochloride is continued to be released from the preparation, absorbed over the whole region of the digestive tract and metabolized to the active metabolite, and, in turn, the active metabolite is continued to be transferred to circulating blood.

However, it is conventionally known that with respect to many drugs, the absorption rate, metabolism rate and the like vary depending on the portion in the digestive tract in which the absorption, metabolism and the like of the drug occur. In some cases, the mode in which the drug is metabolized varies depending on the portion in the digestive tract in which the metabolism of the drug occurs. For this reason, the design for a sustained-release preparation (especially an oral sustained-release preparation) containing a drug which exhibits pharmaceutical activities after being metabolized (such as fasudil hydrochloride) is extremely difficult. In other words, for keeping the concentration of the active metabolite in blood in a desired range for a long period of time, it is extremely difficult to select the releasing pattern of fasudil hydrochloride from the preparation.

In this situation, the present inventors have made extensive and intensive studies with a view toward solving the above-mentioned two problems and developing an oral sustained-release preparation containing fasudil hydrochloride as an active ingredient, which releases a desired amount of fasudil hydrochloride for a long period of time and is capable of maintaining the effects of fasudil hydrochloride for a long period of time. As a result, it has been unexpectedly found that when the oral sustained-release preparation (containing fasudil hydrochloride as an active ingredient) is a preparation comprising at least one sustained-release coated particle comprising a core having a surface and a coating formed on the surface of the core, wherein the core contains the active ingredient and the coating comprises a coating base material and a specific insoluble auxiliary material, it becomes possible to surely control the release of fasudil hydrochloride from the preparation, and that the amount of water present around the above-mentioned preparation has almost no influence on the release of fasudil hydrochloride from the preparation.

Further, it has also been unexpectedly found that when the preparation containing fasudil hydrochloride as an active ingredient exhibits a specific dissolution rate with respect to the active ingredient, as measured by the dissolution test, it becomes possible to keep the concentration of the active metabolite in blood in a desired range for a long period of time.

The present invention has been completed, based on these novel findings.

Accordingly, it is a primary object of the present invention to provide an oral sustained-release preparation containing fasudil hydrochloride as an active ingredient, which releases a desired amount of fasudil hydrochloride for a long period of time and is capable of maintaining the effects of fasudil hydrochloride (exactly, the effects of 1-hydroxy derivative of fasudil hydrochloride) for a long period of time.

It is another object of the present invention to provide a method for evaluating an oral sustainedrelease preparation which contains fasudil hydrochloride as an active ingredient, the evaluation being conducted with respect to the sustained-release ability of the preparation with respect to the fasudil hydrochloride contained therein.

The foregoing and other objects, features and advantages of the present invention will be apparent from the following detailed description taken in connection with the accompanying drawings and the appended claims.

DETAILED DESCRIPTION OF THE INVENTION

Figure 1:
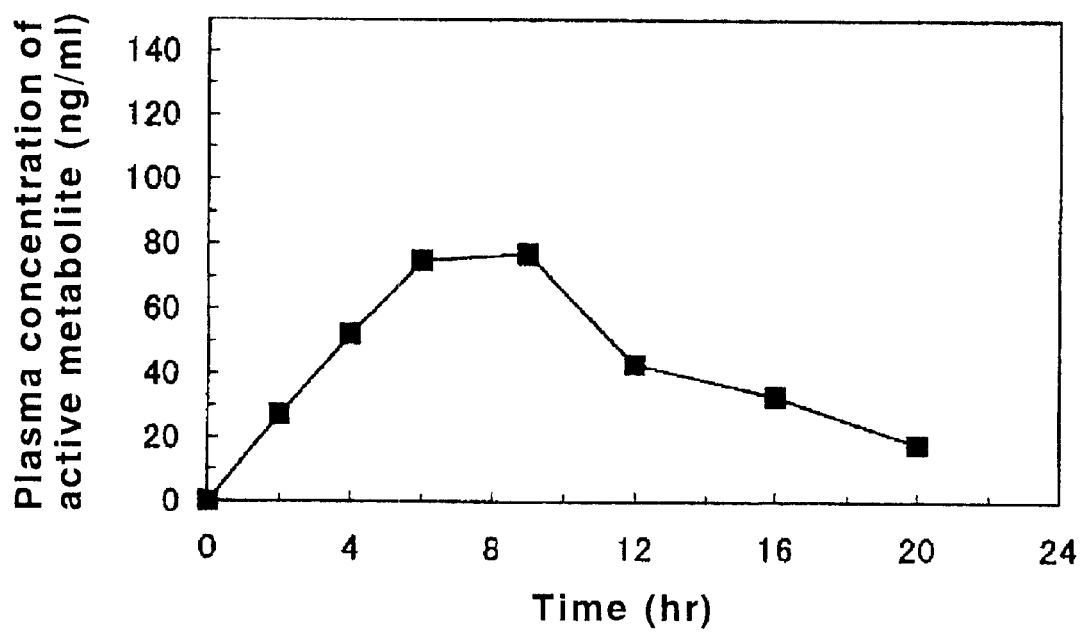
FIG. 1 is a graph showing the change (with the lapse of time) of the plasma concentration of the active metabolite (1-hydroxy derivative of fasudil hydrochloride) in rats, which is obtained by orally administering the oral sustained-release preparation produced in Example 2.

According to the present invention, there is provided an oral sustained-release preparation which contains at least one active ingredient selected from the group consisting of fasudil hydrochloride and a hydrate thereof, wherein the fasudil hydrochloride is represented by the following formula:

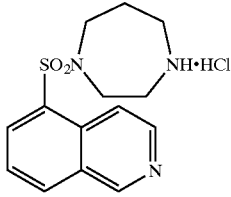

the preparation comprising at least one sustained-release coated particle comprising a core having a surface and a coating formed on the surface of the core, wherein the core contains the active ingredienr and the coating comprises a coating base material and an insoluble auxiliary material which is pharmaceutically acceptable and insoluble in water and ethanol, the preparation exhibiting, with respect to the active ingredient, the following dissolution rates (1), (2) and (3), as measured by method 2 (paddle method) of the dissolution test described in the Japanese Pharmacopoeia Thirteenth Edition:

(1) dissolution of 5 to 40% by weight, based on the weight of the active ingredient originally contained in the preparation, at the point in time of 3 hours after the start of the dissolution test, (2) dissolution of 35 to 70% by weight, based on the weight of the active ingredient originally contained in the preparation, at the point in time of 6 hours after the start of the dissolution test, and (3) dissolution of 70% by weight or more, based on the weight of the active ingredient originally contained in the preparation, at the point in time of 15 hours after the start of the dissolution test.

For easy understanding of the present invention, the essential features and various preferred embodiments of the present invention are enumerated below.

1. An oral sustained-release preparation which contains at least one active ingredient selected from the group consisting of fasudil hydrochloride and a hydrate thereof, wherein the fasudil hydrochloride is represented by the following formula:

the preparation comprising at least one sustained-release coated particle comprising a core having a surface and a coating formed on the surface of the core, wherein the core contains the active ingredient and the coating comprises a coating base material and an insoluble auxiliary material which is pharmaceutically acceptable and insoluble in water and ethanol, the preparation exhibiting, with respect to the active ingredient, the following dissolution rates (1), (2) and (3), as measured by method 2 (paddle method) of the dissolution test described in the Japanese Pharmacopoeia Thirteenth Edition:

(1) dissolution of 5 to 40% by weight, based on the weight of the active ingredient originally contained in the preparation, at the point in time of 3 hours after the start of the dissolution test, (2) dissolution of 35 to 70% by weight, based on the weight of the active ingredient originally contained in the preparation, at the point in time of 6 hours after the start of the dissolution test, and (3) dissolution of 70% by weight or more, based on the weight of the active ingredient originally contained in the preparation, at the point in time of 15 hours after the start of the dissolution test.

2. The oral sustained-release preparation according to item 1 above, wherein the amount of the active ingredient which is contained in the core is at least 30% by weight, based on the weight of the active ingredient contained in the preparation.

3. The oral sustained-release preparation according to item 1 above, wherein the amount of the active ingredient which is contained in the core is substantially 100% by weight, based on the weight of the active ingredient contained in the preparation.

4. The oral sustained-release preparation according to any one of items 1 to 3 above, wherein the coating contains 0.5 to 10 parts by weight of the insoluble auxiliary material, per part by weight of the coating base material.

5. The oral sustained-release preparation according to any one of items 1 to 4 above, wherein the insoluble auxiliary material is at least one member selected from the group consisting of magnesium stearate, calcium stearate, talc, titanium oxide and light anhydrous silicic acid.

6. The oral sustained-release preparation according to any one of items 1 to 5 above, wherein the coating base material is ethylcellulose and the insoluble auxiliary material is talc.

7. The oral sustained-release preparation according to any one of items 1 to 5 above, wherein the coating base material is ethylcellulose and the insoluble auxiliary material is magnesium stearate.

8. The oral sustained-release preparation according to any one of items 1 to 5 above, wherein the coating base material is a copolymer of ethyl acrylate/methyl methacrylate/trimethylammonioethyl methacrylate chloride and the insoluble auxiliary material is talc.

9. An oral sustained-release preparation which contains at least one active ingredient selected from the group consisting of fasudil hydrochloride and a hydrate thereof, wherein the fasudil hydrochloride is represented by the following formula:

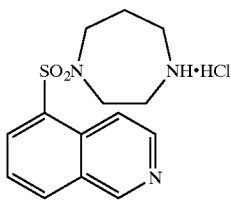

the preparation exhibiting, with respect to the active ingredient, the following dissolution rates (1), (2) and (3), as measured by method 2 (paddle method) of the dissolution test described in the Japanese Pharmacopoeia Thirteenth Edition:
(1) dissolution of 5 to 40% by weight, based on the weight of the active ingredient originally contained in the preparation, at the point in time of 3 hours after the start of the dissolution test,
(2) dissolution of 35 to 70% by weight, based on the weight of the active ingredient originally contained in the preparation, at the point in time of 6 hours after the start of the dissolution test, and
(3) dissolution of 70% by weight or more, based on the weight of the active ingredient originally contained in the preparation, at the point in time of 15 hours after the start of the dissolution test.

10. A method for evaluating an oral sustained-release preparation containing at least one active ingredient selected from the group consisting of fasudil hydrochloride and a hydrate thereof, wherein the fasudil hydrochloride is represented by the following formula:

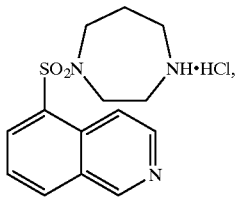

the evaluation being conducted with respect to the sustained-release ability of the preparation with respect to the fasudil hydrochloride contained therein,
the method comprising subjecting the preparation to a testing according to a dissolution test method, the testing providing substantially the same evaluation as the evaluation obtained by conducting a standard testing according to method 2 (paddle method) of the dissolution test described in the Japanese Pharmacopoeia Thirteenth Edition and assessing a dissolution of the active ingredient from the preparation by taking as a criterion the following dissolution rates (1), (2) and (3):
(1) dissolution of 5 to 40% by weight, based on the weight of the active ingredient originally contained in the preparation, at the point in time of 3 hours after the start of the,dissolution test,
(2) dissolution of 35 to 70% by weight, based on the weight of the active ingredient originally contained in the preparation, at the point in time of 6 hours after the start of the dissolution test, and
(3) dissolution of 70% by weight or more, based on the weight of the active ingredient originally contained in the preparation, at the point in time of 15 hours after the start of the dissolution test.

Hereinbelow, the present invention is described in detail.

The oral sustained-release preparation of the present invention contains at least one active ingredient selected from the group consisting of fasudil hydrochloride and a hydrate thereof, wherein the fasudil hydrochloride is represented by the following formula:

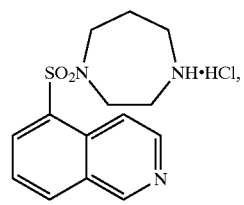

Fasudil hydrochloride (anhydride) can be produced by a conventional method, for example, the method described in Examined Japanese Patent Application Publication No. 5-3851 (corresponding to U.S. Pat. No. 4,678,783).

Further, a fasudil hydrochloride hydrate can be produced by a conventional method, for example, the method described in International Patent Application Publication No. WO 97/02260 (corresponding to EP 0 870 767 A1). As fasudil hydrochloride hydrates, there are known, for example, fasudil hydrochloride hemihydrate and fasudil hydrochloride trihydrate. In the present invention, any of the known fasudil hydrochloride hydrates can be employed.

In the oral sustained-release preparation of the present invention, it is preferred that the active ingredient is selected from the group consisting of fasudil hydrochloride anhydride and fasudil hydrochloride hemihydrate.

In the present invention, when it is necessary to convert the weight of a fasudil hydrochloride hydrate to the weight of fasudil hydrochloride anhydride or vice versa, the conversion of the weight can be easily achieved, using the molecular weight ratio between the anhydride and the hydrate (wherein the molecular weight of the water of hydration is also taken into consideration). For example, by multiplying the weight of fasudil hydrochloride hemihydrate by 0.9733, the weight can be converted into the weight of fasudil hydrochloride anhydride.

The oral sustained-release preparation of the present invention comprises at least one sustained-release coated particle comprising a core having a surface and a coating formed on the surface of the core.

The above-mentioned term "particle" is used as a general term covering various particles of various sizes, such as granules, powder and pills. In the present invention, it is preferred that the sustained-release coated particle is a granule.

The oral sustained-release preparation of the present invention may comprise only one sustained-release coated particle. However, it is preferred that the oral sustained-release preparation of the present invention comprises several sustained-release coated particles.

The above-mentioned core contains the above-mentioned active ingredient. Specifically, the above-mentioned core contains at least a part of the above-mentioned active ingredient. When the oral sustained-release preparation comprises a plurality of sustained-release coated particles each containing the core, the plurality of cores collectively contain at least a part of the above-mentioned active ingredient.

With respect to the weight ratio of the active ingredient which is contained in the core to the entire active ingredient contained in the oral sustained-release preparation of the present invention, there is no particular limitation. However, from the viewpoint of rendering uniform the quality of the oral sustained-release preparation and preventing the occurrence of a variation in amount of the active ingredient released from the preparation and absorbed by the body, it is preferred that the above-mentioned weight ratio is as large as possible. In the present invention, it is preferred that the weight ratio of the active ingredient which is contained in the core is at least 30% by weight, more advantageously at least 60% by weight, still more advantageously at least 80% by weight, most advantageously substantially 100% by weight, based on the weight of the active ingredient contained in the oral sustained-release preparation. The above-mentioned term "substantially 100% by weight" means ordinarily 95% by weight or more, preferably 100% by weight.

With respect to the content of the active ingredient in the core, there is no particularly limitation. However, it is preferred that the content of the active ingredient in the core is 30% by weight or more, more advantageously 50% by weight or more, based on the weight of the core. The core may consist only of the active ingredient.

The amount of the active ingredient is defined as the weight of fasudil hydrochloride anhydride. That is, when a fasudil hydrochloride hydrate is used as the active ingredient, the weight of an equimolar amount of fasudil hydrochloride anhydride is taken as the amount of the active ingredient.

With respect to the size of the core, there is no particularly limitation. However, it is preferred that the core has an average particle diameter which is 100 $\mu$m or more, more advantageously 300 $\mu$m or more, especially advantageously 500 $\mu$m or more. It is also preferred that the average particle diameter of the core is 5,000 $\mu$m or less, more advantageously 2,000 $\mu$m or less, still more advantageously 1,500 $\mu$m or less, especially advantageously 1,000 $\mu$m or less.

The coating formed on the surface of the core comprises a coating base material and an insoluble auxiliary material which is pharmaceutically acceptable and insoluble in water and ethanol.

With respect to the coating base material used in the present invention, there is no particularly limitation as long as it is pharmaceutically acceptable and capable of forming a coating. Examples of coating base materials include hydrophobic polymers and hydrophilic polymers. These polymers can be used individually or in combination.

In the case of the coating base material composed of a hydrophobic polymer, after the oral sustained-release preparation of the present invention has been administered, the internal liquid of the digestive tract permeates into and through the coating of the sustained-release coated particle, so that the liquid contacts the core in the particle. It is presumed that, as a result, the active ingredient in the core is dissolved in the liquid and the resultant solution permeates through the coating, so that the active ingredient is released from the sustained-release coated particle.

In the case of the coating base material composed of a hydrophilic polymer, after the oral sustained-release preparation of the present invention has been administered, the internal liquid of the digestive tract contacts and gradually dissolves or decomposes the coating of the sustained-release coated particle, so that a part of the surface of the core in the particle is caused to contact the liquid. It is presumed that, as a result, the active ingredient in the core is dissolved in the liquid and released from the sustained-release coated particle.

Examples of hydrophobic polymers include cellulose ethers, such as ethylcellulose and butylcellulose, cellulose esters, such as cellulose acetate and cellulose propionate, polyvinyl esters, such as polyvinyl acetate and polyvinyl butyrate, and synthetic acrylic polymers, such as a copolymer of ethyl acrylate/methyl methacrylate/trimethylammonioethyl methacrylate chloride. These hydrophobic polymers can be used individually or in combination. Among these hydrophobic polymers, preferred are ethylcellulose, cellulose acetate and a copolymer of ethyl acrylate/methyl methacryate/trimethylammonioethyl methacrylate chloride.

Hydrophilic polymers can be selected from water-soluble polymers, polymers soluble in intestine (enteric polymers), polymers soluble in stomach (stomach-soluble polymers) and polymers soluble in both stomach and intestine (stomach/intestine-soluble polymers).

Examples of water-soluble polymers include pullulan, dextrin, hydroxypropylcellulose, hydroxypropylmethylcellulose, carboxymethylcellulose, methylcellulose, polyvinylpyrrolidone, polyvinyl alcohol and polyethylene glycol. These water-soluble polymers can be used individually or in combination. Among these water-soluble polymers, preferred are hydroxypropylcellulose and hydroxypropylmethylcellulose.

The above-mentioned "enteric polymers" are polymeric substances which are insoluble or stable under acidic conditions exhibiting a pH of less than 5 and which are dissolved or decomposed under conditions exhibiting a pH of 5 or more. Examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethyl cellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleid acid monoester, a copolymer of methyl acrylate/methacrylic acid, a copolymer of styrene/acrylic acid, a copolymer of methyl acrylate/methacrylic acid/octyl acrylate and a copolymer of methacrylic acid/methyl methacrylate. These enteric polymers can be used individually or in combination. Among these enteric polymers, preferred are carboxymethylethylcellulose, hydroxypropylmethylcellulose acetate succinate and a copolymer of methacrylic acid/methyl methacrylate.

The above-mentioned "stomach-soluble polymers" are polymeric substances which are insoluble or stable under weakly acidic or basic conditions exhibiting a pH of more than 6 and which are dissolved or decomposed under conditions exhibiting a pH of 6 or less. Examples of such stomach-soluble polymers include benzylaminomethylcellulose, diethylaminomethylcellulose, piperidylethylhydroxyethylcellulose, cellulose acetate dimethylaminoacetate, a copolymer of vinyl diethylamine/vinyl acetate, a copolymer of vinyl benzylamine/vinyl acetate, polyvinyl acetal diethylamino acetate, a copolymer of vinylpiperidyl acetoacetal/vinyl acetate, polydiethylaminomethylstyrene, a copolymer of methyl methacrylate/butyl methacrylate/dimethylaminoethyl methacrylate and polydimethylaminoethyl methacrylate. These stomach-soluble polymers can be used individually or in combination. Among these stomach-soluble polymers, preferred are polyvinyl acetal diethylaminoacetate and a copolymer of methyl meth acrylate/butyl methacrylate/dimethylaminoethyl methacrylate.

The above-mentioned "stomach/intestine-soluble polymers" are polymeric substances which are insoluble or stable under conditions exhibiting a pH of from more than 4.5 to less than 6 and which are dissolved or decomposed under conditions exhibiting a pH of 4.5 or less or a pH of 6 or more. Examples of such stomach/intestine-soluble polymers include a copolymer of 2-methyl-5-vinylpyridine/methyl methacrylate/methacrylic acid, a copolymer of 2-methyl-5-vinylpyridine/methyl acrylate/methacrylic acid, a copolymer of 2-vinyl-5-ethylpyridine/methacrylic acid/styrene, a copolymer of 2-vinyl-5-ethylpyridine/methacrylic acid/methyl acrylate, a copolymer of 2-vinylpyridine/methacrylic acid/methyl acrylate, a copolymer of 2-vinylpyridine/methacrylic acid/acrylonitrile, carboxymethylpiperidyl starch, carboxymethylbenzylaminocellulose, poly(2-vinylphenylglycine) and a copolymer of N-vinylglycine/styrene. These stomach/intestinesoluble polymers can be used individually or in combination.

As mentioned above, the insoluble auxiliary material used in the present invention is a material which is pharmaceutically acceptable and insoluble in water and ethanol. Herein, the term "insoluble" is intended to mean being "practically insoluble" in the meaning as defined in item 23 of the General Notices of the Japanese Pharacopoeia Thirteenth Edition. That is, the term "insoluble" is intended to mean that dissolution of 1 g or 1 ml of a certain substance in a certain solvent needs 10,000 ml or more of the solvent under given conditions.

Examples of insoluble auxiliary materials include talc, titanium oxide, magnesium stearate, calcium stearate and light anhydrous silicic acid. Of these, talc and magnesium stearate are preferred.

With respect to the amount of the insoluble auxiliary material, there is no particular limitation. However, it is preferred that the lower limit of the amount of the insoluble auxiliary material is 0.5 part by weight, more advantageously 0.7 part by weight, still more advantageously 1 part by weight, per part by weight of the coating base material. On the other hand, it is preferred that the upper limit of the amount of the insoluble auxiliary material is 10 parts by weight, more advantageously 7 parts by weight, still more advantageously 5 parts by weight, per part by weight of the coating base material.

It is preferred that the insoluble auxiliary material is in the form of a fine powder or fine particles. When the insoluble auxiliary material is in the form of a fine powder or fine particles, it is preferred that the lower limit of the average particle diameter of the insoluble auxiliary material is 0.1 $\mu$m, more advantageously 0.3 $\mu$m, still more advantageously 0.5 $\mu$m. On the other hand, it is also preferred that the upper limit of the average particle diameter of the insoluble auxiliary material is 300 $\mu$m, more advantageously 100 $\mu$m, still more advantageously 50 $\mu$m.

With respect to the combination of the types of the coating base material and the insoluble auxiliary material, there is no particular limitation. However, preferred are the following combinations: a combination wherein the coating base material is ethylcellulose and the insoluble auxiliary material is talc, a combination wherein the coating base material is ethylcellulose and the insoluble auxiliary material is magnesium stearate, and a combination wherein the coating base material is a copolymer of ethyl acrylate/methyl methacrylate/trimethylammonioethyl methacrylate chloride and the insoluble auxiliary material is talc.

Further, it is preferred that the above-mentioned coating is uniformly formed on the surface of the core. The thickness of the above-mentioned coating is not particularly limited, but is preferably in the range of from 5 to 100 $\mu$m, more preferably from 10 to 50 $\mu$m.

In the present invention, there is no particular limitation with respect to the method for producing the sustained-release coated particle. However, as an example of method for producing the sustained-release coated particle, there can be mentioned a method comprising preparing a core member containing at least one active ingredient selected from the group consisting of fasudil hydrochloride and a hydrate thereof, and forming, on the surface of the obtained core member, a coating comprising the above-mentioned coating base material and the above-mentioned insoluble auxiliary material. With respect to this method for producing the sustained-release coated particle, a more specific explanation is made below.

With respect to the shape of the core member, there is no particular limitation. However, it is preferred that the core member has a spherical shape. There is also no particular limitation with resect to the size of the core member. However, with respect to the average particle diameter of the core member, the lower limit is preferably 100 $\mu$m, more preferably 300 $\mu$m, especially preferably 500 $\mu$m, and the upper limit is preferably 5,000 $\mu$m, more preferably 2,000 $\mu$m, still more preferably 1,500 $\mu$m, especially preferably 1,000 $\mu$m.

There is no particular limitation with respect to the method for producing the core member. However, as examples of methods for producing the core member, there can be mentioned the following methods:

(a) a method in which, using a centrifugal rolling granulator, a rolling fluid-bed granulator, a fluid-bed granulator or the like, the surface of the below-described nucleating excipient is applied with a fasudil hydrochloride-containing solution or suspension, while evaporating the solvent contained in the solution or suspension applied to the surface of the nucleating excipient by heated air to thereby form a fasudil hydrochloride coating on the surface of the nucleating excipient and effect granulation, followed by drying to obtain a core member:

(b) a method in which, using the above-mentioned granulator, the surface of the below-described nucleating excipient is applied with a powdery fasudil hydrochloride to thereby form a fasudil hydrochloride coating on the surface of the nucleating excipient and effect granulation, followed by drying to obtain a core member: and (c) a method in which, using a fluid-bed granulator, an extrusion granulator or the like, a powdery fasudil hydrochloride is granulated by the direct granulation method without using a nucleating excipient and then, if desired, the resultant granule is rendered spherical using a spheronizer, thereby obtaining a core member.

The above-mentioned nucleating excipient functions as a nucleus for forming a granule by coating the surface of it with a drug. The nucleating excipient is in a particulate form and is obtained by granulating a pharmaceutically acceptable excipient. As an example of commercially available nucleating excipients, there can be mentioned a nucleating excipient comprising sucrose, starch, a crystalline cellulose, or a mixture thereof.

Further, the production of the above-mentioned core member may be conducted in the presence of a binder. Preferred examples of binders include methylcellulose, hydroxypropylcellulose, hydroxypropylmethylcellulose and polyvinylpyrrolidone.

With respect to the method for forming, on the surface of the core member, a coating comprising the above-mentioned coating base material and the above-mentioned insoluble auxiliary material, there is no particular limitation. For example, using a centrifugal rolling granulator, a rolling fluid-bed granulator, a fluid-bed granulator or the like, the coating can be formed as follows. First, the above-mentioned coating base material is dissolved or dispersed in a solvent, such as water, ethanol, methylene chloride or acetone, and in the resultant solution or dispersion, the above-mentioned insoluble auxiliary material is dispersed, to thereby obtain a coating liquid. Then, using a fluidbed granulator or the like, the coating liquid is coated on the surface of the core member, while evaporating the solvent contained in the coating solution coated on the core member by heated air, to thereby obtain a sustained-release coated particle.

In the present invention, if desired, the sustained-release coated particle may further contain, in the core and/or coating thereof, a pharmceutically acceptable excipient, binder, disintegrant, corrigent, pH-adjusting agent, lubricant, thickening agent, coloring agent or the like.

Using the thus prepared sustained-release coated particle, the oral sustained-release preparation of the present invention can be obtained by, for example, a method in which the sustained-release coated particle is encapsulated to thereby obtain the oral sustained-release preparation of the present invention in the form of a capsule, or a method in which the sustained-release coated particle is tableted to thereby obtain the oral sustained-release preparation of the present invention in the form of a tablet. Further, the sustained-release coated particle as such can also be used as the oral sustained-release preparation of the present invention. In this case, the sustained-release coated particle can be used in various forms, such as granule, powder and pill. With respect to the form of the oral sustained-release preparation of the present invention, it is preferred that the preparation is in the form of a capsule or a granule (each of a powder and a pill is also regarded as a granule).

Further, with respect to the method for obtaining the preparation of the present invention in the form of a tablet, reference can be made to the description of Yoshiaki Kawashima et al. ("Huntai no asshuku seikei gijutsu (Method for compression-molding a powder)", p. 172, Shinji Aoki et al., edited by the committee for Pharmaceutical Preparations and Particle Design, The Society of Powder Technology, Japan, published by The Nikkan Kogyo Shinbun, Ltd., Japan, 1998).

The content of the active ingredient in the oral sustained-release preparation of the present invention may vary depending on the types and amounts of other ingredients, the indication (namely, disease-suffering and treatment-needing patient condition) of the preparation and the like, and, hence, is not particularly limited. For example, when the preparation of the present invention, which can be used for the treatment of various diseases, is used for the treatment of an ischemic disease, such as angina pectoris, the content of the active ingredient in the preparation of the present invention per dose of the preparation is generally 1 to 1,000 mg, preferably 15 to 300 mg, in terms of the weight of fasudil hydrochloride hemihydrate.

If desired, the oral sustained-release preparation may further contain a pharmceutically acceptable excipient, binder, disintegrant, corrigent, pH-adjusting agent, lubricant, thickening agent, aromatizing agent, coloring agent or the like.

The oral sustained-release preparation may comprise at least two different types of sustain-release coated particles, which have different sustain-release properties. Further, the oral sustained-release preparation may further comprise a rapid-release particle containing the above-mientioned active ingredient. The above-mentioned rapid-release particles means a particle capable of rapidly releasing the active ingredient. Examples of rapid-release particles include the above-mentioned core members as such, e.g., the core member composed only of the active ingredient, which can be obtained by the above-mentioned method (c); and rapid-release particles obtained by coating such a core member in accordance with conventional methods or methods similar to the above-mentioned method for coating the core member, wherein appropriate coating conditions or coating materials are selected so as to obtain a rapid-release particle.

When the oral sustained-release preparation of the present invention comprises at least two different types of sustained-release coated particles, or contains the sustained-release coated particles and the rapid-release particles, the weight ratio of the particles can be determined by, for example, the following method.

With respect to the oral sustained-release preparation of the present invention containing n different types of particles $K_1, K_2 \ldots K_i \ldots K_n$, let us assume:

that the weight ratio of particle $K_i$ to the total weight of particles $K_1, K_2 \ldots K_i \ldots K_n$ is defined as $X_i$, that the weight ratio of the active ingredient contained in particle $K_i$ to the weight of particle $K_i$ is defined as $Z_i$, and that the weight ratio of the active ingredient contained in particle $K_i$ to the total weight of the active ingredients which are, respectively, contained in particles $K_1, K_2 \ldots K_i \ldots K_n$ (i.e., the total weight of the active ingredients originally contained in the oral sustained-release preparation of the present invention) is defined as $Y_i$.

Then, the following relationship can be obtained:

$$Y_1 : Y_2 : \ldots : Y_i : \ldots : Y_n = X_1 \times Z_1 : X_2 \times Z_2 : \ldots X_i \times Z_i : \ldots : X_n \times Z_n.$$

Therefore, $X_i = Y_i / Z_i$ \hfill (a).

Further, with respect to particle $K_i$, by the below-described paddle method of the dissolution test (or a method which can be used for obtaining substantially the same results as in the paddle method), the dissolution rates ($Q_{i3}$, $Q_{i6}$ and $Q_{i15}$) of the active ingredient at the points in time of 3, 6 and 15 hours after the start of the dissolution test are measured.

Then, with respect to particles $K_1, K_2 \ldots K_i \ldots K_n$, $Y_i$ values satisfying all of the following requiquirements (I), (II) and (III) are appropriately chosen.

$$5 \leq \sum_{i=1}^{n} Y_i Q_{i3} \leq 40 \quad \text{(I)}$$

$$35 \leq \sum_{i=1}^{n} Y_i Q_{i6} \leq 70 \quad \text{(II)}$$

$$70 \leq \sum_{i=1}^{n} Y_i Q_{i15} \quad \text{(III)}$$

Using the obtained $Y_i$ values and $Z_i$ values, $X_i$ values can be calculated in accordance with formula (a) above.

In this instance, it is noted that the amount of the active ingredient is defined as the weight of fasudil hydrochloride anhydride. That is, as mentioned above, when a fasudil hydrochloride hydrate is used as the active ingredient, the weight of an equimolar amount of fasudil hydrochloride anhydride is taken as the amount of the active ingredient.

The preparation of the present invention exhibits, with respect to the active ingredient, the following dissolution rates (1), (2) and (3), as measured by method 2 (paddle method) of the dissolution test described in the Japanese Pharmacopoeia Thirteenth Edition:

(1) dissolution of 5 to 40% by weight, based on the weight of the active ingredient originally contained in the preparation, at the point in time of 3 hours after the start of the dissolution test, (2) dissolution of 35 to 70% by weight, based on the weight of the active ingredient originally contained in the preparation, at the point in time of 6 hours after the start of the dissolution test, and (3) dissolution of 70% by weight or more, based on the weight of the active ingredient originally contained in the preparation, at the point in time of 15 hours after the start of the dissolution test.

The above-mentioned method 2 (hereinafter referred to simply as "paddle method") of the dissolution test is described in the Japanese Pharmacopoeia Thirteenth Edition (adopted since 1996) under the section "General Tests". Hereinbelow, an explanation will be made on one mode for performing the dissolution test by the paddle method (an English version of the Japanese Pharmacopoeia Thirteenth Edition (published in 1996) is available from Yakuji Nippo, Ltd., Japan).

In the explanation made below, the amount of the active ingredient is defined as the weight of fasudil hydrochloride anhydride. That is, as mentioned above, when a fasudil hydrochloride hydrate is used as the active ingredient, the weight of an equimolar amount of fasudil hydrochloride anhydride is taken as the amount of the active ingredient.

There is no particular limitation with respect to the apparatus used for conducting the dissolution test as long as the apparatus is in conformity with the Japanese Pharmacopoeia and the dissolution test by the paddle method.

First, 900 ml of a dissolution medium (deaerated by a suitable method) is added to a vessel of the dissolution test apparatus, and the temperature of the dissolution medium is maintained at 37±0.5° C. Usually, when the oral sustained-release preparation of the present invention is subjected to the dissolution test, distilled water is used as the dissolution medium. With respect to the method for deaerating the dissolution medium, there is no particular limitation, and the deaeration of the dissolution medium can be conducted by placing the dissolution medium under reduced pressure, by subjecting the dissolution medium to ultrasonication, or by subjecting the dissolution medium to ultrasonication under reduced pressure. Such a deaeration treatment is usually conducted for 5 to 10 minutes.

Next, a paddle is attached to the apparatus, and a sample of the oral sustained-release preparation of the present invention is allowed to sink to the center of the bottom of the vessel. The revolution of the paddle is started immediately after the sample reaches the bottom of the vessel. The revolution rate of the paddle is adjusted to 100±4 revolutions per minute. During the subsequent steps, the opening of the vessel is covered to prevent the evaporation of the dissolution medium.

Usually, one dose of the oral sustained-release preparation of the present invention is used as a sample for the dissolution test. For example, when the oral sustained-release preparation is in the form of a tablet or a capsule, one tablet or one capsule is used as a sample. When such a preparation floats in the dissolution medium, the preparation is placed in a sinker specified in the Japanese Pharmacopoeia, and allowed to sink to the center of the bottom of the vessel. When the oral sustained-release preparation is in the form of granules, a powder and the like, one dose of the preparation is measured and added directly to the dissolution medium in the vessel. Usually, in this case, there is no need to use a sinker.

At the points in time of at least 3, 6 and 15 hours, preferably 1, 2, 3, 4, 6, 8, 10, 12, 15 and 20 hours after the start of the dissolution test (namely after the start of the revolution of the paddle), 10 ml of the dissolution medium containing the active ingredient released from the preparation (hereinafter, referred to as an "active ingredient-dissolved solution") is collected from the vessel at a position which is intermediate between the surface of the dissolution medium and the top of the paddle, and 10 mm distant from the inner wall of the vessel. Immediately after collecting the active ingredient-dissolved solution, 10 ml of distilled water heated to 37±0.5° C. is carefully added to the vessel to thereby compensate for the dissolution medium taken from the vessel. The collected active ingredient-dissolved solution is filtered using a membrane filter (pore size: 0.5 μm) and the resultant filtrate is used as a sample solution.

Apart from the above operation, a standard fasudil hydrochloride solution having a known concentration of fasudil hydrochloride is prepared by dissolving a predetermined amount of a standard fasudil hydrochloride in distilled water, followed by adjusting the volume of the aqueous fasudil hydrochloride solution to 1,000 ml. With respect to the sample solution and the standard fasudil hydrochloride solution, an absorbance at 275 nm (hereinafter referred to simply as the "absorbance") is measured.

When the 1st, 2nd, . . . and n-th (n is an integer of 3 or more) sample solutions are respectively collected at the points in time of $t_1$ hr, $t_2$ hr, . . . and $t_n$ hr in the above-mentioned manner, the weight percent (%) of the dissolved active ingredient contained in the active ingredient-dissolved solution, based on the weight of the active ingredient originally contained in the preparation (hereinafter referred to simply as a "dissolution rate") can be calculated as follows, taking as an example a dissolution rate at the point in time of collecting the 1st sample solution, that is, at the point in time of $t_1$ hours after the start of the dissolution test:

Dissolution rate at the point in time of $t_1$ hr from the start of the dissolution test $(\%) = 100 \times \{m_s \times A_1 \div (A_s \times 1000 \div 900) \div m_t\}$ wherein:

$m_t$: total weight of the active ingredient originally contained in the preparation;

$m_s$: weight of the active ingredient used for preparing the standard solution;

$A_1$: absorbance of the 1st sample solution; and $A_s$: absorbance of the standard solution.

Further, the dissolution rate (%) at the point in time of collecting the i-th (i represents an integer of from 2 to n) sample solution, that is, at the point in time of $t_i$ hr after the start of the dissolution test, can be calculated by the following formula:

Dissolution rate (%) at the point in time of $t_i$ hr from the start of the dissolution test =

$$100 \times \left\{ m_s \times \left( A_i + \sum_{j=1}^{i-1} A_j \times 10 \div 900 \right) \div (A_s \times 1000 \div 900) \div m_t \right\}$$

wherein:

$m_t$: total weight of the active ingredient originally contained in the preparation;

$m_s$: weight of the active ingredient used for preparing the standard solution;

$A_i$: absorbance of the i-th sample solution;

$A_s$: absorbance of the standard solution; and $\sum_{j=1}^{i-1} A_j$: sum of the absorbances of the 1st to $(i-1)$-th sample solutions.

Usually, the above-mentioned test is repeated six times, and the mean value of the dissolution rates obtained at the point in time of $t_1$ hours after the start of the dissolution tests is determined.

As mentioned above, with respect to the oral sustained-release preparation of the present invention, the dissolution rates (mean values) of the active ingredient determined by the above-mentioned method at the points in time of 3, 6 and 15 hours after the start of the dissolution test satisfy the above-mentioned dissolution rate requirements (1), (2) and (3), respectively.

With respect to the oral sustained-release preparation of the present invention, it is preferred that the dissolution rate at the point in time of 3 hours after the start of the dissolution test is 5 to 35% by weight, based on the weight of the active ingredient originally contained in the preparation.

Further, it is preferred that the dissolution rate at the point in time of 6 hours after the start of the dissolution test is not lower than the dissolution rate at the point in time of 3 hours after the start of the dissolution test, and the dissolution rate at the point in time of 15 hours after the start of the dissolution test is not lower than the dissolution rate at the point in time of 6 hours after the start of the dissolution test.

Methods other than the paddle method mentioned above can be used to evaluate the dissolution rate of the active ingredient of the oral sustained-release preparation of the present invention, with the proviso that such methods provide substantially the same evaluation as obtained by the paddle method. Examples of other methods include, method 1 (rotary basket method) and method 3 (flow-through method) of the Japanese Pharmacopoeia Thirteenth Edition; a method described under the section "Dissolution" at page 1791 of The United States Pharmacopoeia XXIII Edition (adopted since 1995), which uses "Apparatus 2", and other methods conducted in accordance with this method; and a method described under the section "2.9.3. Dissolution Test for Solid Dosage Forms" at page 128 of the European Pharmacopoeia Third Edition (adopted since 1997), which uses "Paddle apparatus", and other methods conducted in accordance with this method.

The oral sustained-release preparation of the present invention is orally administered. The dose of the oral sustained-release preparation of the present invention may widely vary depending on the types and the amounts of the components of the preparation, the disease to be treated with the preparation, and the conditions, age and sex of the patient. When the oral sustained-release preparation of the present invention is used for treating an ischemic disease (such as angina pectoris), a suitable amount of the oral sustained-release preparation per dose is selected within the range of from 1 to 1,000 mg, preferably 15 to 300 mg, in terms of the weight of fasudil hydrochloride hemihydrate, and the preparation is orally administered to an adult patient once or twice a day or once in two days.

BEST MODE FOR CARRYING OUT THE INVENTION

Hereinbelow, the present invention will be described in more detail with reference to the following Reference Examples, Examples, Comparative Examples and Experiments, which should not be construed as limiting the scope of the present invention.

In the following Reference Examples, Examples and Comparative Examples, in addition to fasudil hydrochloride (used as an active ingredient), the following materials were used for producing pharmaceutical preparations.

1) Nucleating Excipient (Excipient in the Form of Fine Particles)

NONPAREIL 105 (spherical granules of lactose and crystalline cellulose (particle diameter: 500 to 710 μm)) (manufactured and sold by Freund Industrial Co., Ltd., Japan).

CELPHERE CP-507 (granules of crystalline cellulose (particle diameter: 500 to 710 μm)) (manufactured and sold by Asahi Kasei Kogyo KabushiKi Kaisha, Japan).

2) Coating Base Material

Ethylcellulose (grade: 10 cps) (manufactured and sold by Dow Chemical Company, USA).

Eudragit RLPO (a copolymer of ethyl acrylate/methyl methacrylate/trimethylammonioethyl methacrylate chloride) (manufactured and sold by RÖHM GmbH, Germany).

Eudragit RSPO (a copolymer of ethyl acrylate/methyl methacrylate/trimethylammonioethyl methacrylate chloride (wherein the contents of the comonomer units are different from those of Eudragit RLPO mentioned above)) (manufactured and sold by RÖHM GmbH, Germany).

Aquacoat (an aqueous dispersion of ethylcellulose) (manufactured and sold by Asahi Kasei Kogyo Kabushiki Kaisha, Japan).

3) Insoluble Auxiliary Material

Talc (in conformity with the Japanese Pharmacopoeia; average particle diameter: 11.0 μm) (manufactured and sold by Hayashi Chemical Co., Ltd., Japan).

Magnesium stearate (in conformity with the Japanese Pharmacopoeia; average particle diameter: 11.3 μm) (manufactured and sold by Taihei Chemical Co., Ltd., Japan).

Titanium oxide (anatase type) (manufactured and sold by Wako Pure Chemical Industries, Ltd., Japan).

4) Other Materials

HPC-L (hydroxypropylcellulose) (manufactured and sold by Nippon Soda Co., Ltd., Japan).

Triethyl citrate (manufactured and sold by Pfizer Pharmaceuticals Inc., Japan).

TC-5R (hydroxypropylmethylcellulose 2910) (manufactured and sold by Shin-Etsu Chemical Ind. Co., Ltd., Japan).

D-mannitol (manufactured and sold by TOWA CHEMICAL INDUSTRY CO., LTD., Japan).

NS-300 (carmellose) (manufactured and sold by Gotoku Chemical Co., Ltd., Japan).

AVICEL PH301 (crystalline cellulose) (manufactured and sold by Asahi Kasei Kogyo KabushiKi Kaisha, Japan).

ADOSOLIDER 101 (light anhydrous silicic acid) (manufactured and sold by Freund Industrial Co., Ltd., Japan).

TC-5RW (hydroxypropylmethylcellulose 2910; a white substance obtained by depigmenting TC-5R mentioned above) (manufactured and sold by Shin-Etsu Chemical Ind. Co., Ltd., Japan).

Polishing WAX 103 (carnauba wax) (manufactured and sold by Freund Industrial Co., Ltd., Japan).

Corn starch (manufactured and sold by NIHON SHOKUHIN KAKO CO., LTD., Japan).

PRIMOJEL (sodium carboxylmethylstarch) (manufactured and sold by Matsutani Chemical Industry Co., Ltd., Japan).

Ethanol (in conformity with the Japanese Pharmacopoeia) (manufactured and sold by Wako Pure Chemical Industries, Ltd., Japan).

Capsule No. 1 (in conformity with the Japanese Pharmacopoeia) (manufactured and sold by Shionogi Qualicaps Co., Ltd., Japan).

Capsule No. 2 (in conformity with the Japanese Pharmacopoeia) (manufactured and sold by Shionogi Qualicaps Co., Ltd., Japan).

Capsule No. 3 (in conformity with the Japanese Pharmacopoeia) (manufactured and sold by Shionogi Qualicaps Co., Ltd., Japan).

In the Experiments described below, the concentration of the drug in the blood of rats was determined by the below-mentioned method using high performance liquid chromatography (HPLC). Illustratively stated, a sample for HPLC was prepared as described in item (1) below, and HPLC was performed under the conditions described in item (2) below. By the below-mentioned method, only 1-hydroxy derivative of fasudil hydrochloride (i.e., active metabolite) was detected, and other metabolites or unchanged fasudil hydrochloride was not detected.

(1) Preparation of a Sample for HPLC 1 ml of blood was collected from a rat and subjected to centrifugation to thereby obtain a supernatant (i.e., plasma). The obtained plasma was diluted with 8 ml of distilled water, and the diluted plasma was applied to a solid-phase extraction column (Bond Elut CBA; manufactured and sold by GL Sciences Inc., Japan) which had previously been conditioned first with 3 ml of methanol and then with 3 ml of distilled water. Then, the column was washed first with 3 ml of distilled water and then with 9 ml of methanol, to thereby elute most of substances other than the active metabolite. Subsequently, the column was washed with 4 ml of methanol containing 2% of concentrated ammonia water, thereby obtaining a fraction containing the active metabolite. The obtained fraction was evaporated to dryness by means of a centrifugal evaporator, and the resultant solid was dissolved in 200 µl of a mixture of 50 mM phosphate buffer (pH 6.8) and methanol (phosphate buffer:methanol=9:1 (v/v)), thereby obtaining a solution. The solution was subjected to filtration using a filter, and the resultant filtrate was used as an HPLC sample.

(2) Apparatus and Conditions for HPLC

Apparatus: D7000 model HPLC system (manufactured and sold by Hitachi, Ltd., Japan)

Column: YMC AM-302 (manufactured and sold by YMC Co., Ltd., Japan.)

Column temperature: 30° C.

Mobile phase: a mixture of 50 mM phosphate buffer (pH 6.8) and acetonitrile (phosphate buffer:acetonitrile= 85:15 (v/v))

Flow rate: 0.5 ml/min.

UV detector: L-7400 model UV detector (manufactured and sold by Hitachi, Ltd., Japan)

Detection wavelength: 300 nm

Volume of a sample applied: 100 µl

REFERENCE EXAMPLE 1

400 g of fasudil hydrochloride anhydride was dissolved in 600 ml of purified water to obtain an aqueous solution of fasudil hydrochloride. Using the obtained aqueous solution of fasudil hydrochloride, 350 g of NONPAREIL 105 was subjected to coating with fasudil hydrochloride by the Wurster method in the following manner. That is, 350 g of NONPAREIL 105 was charged into a LAB-1 model fluid-bed granulator (manufactured and sold by POWREX CORPORATION, Japan), which was equipped with a sprayer. The aqueous solution of fasudil hydrochloride was charged in the sprayer of the granulator. The NONPAREIL 105 was subjected to fluidization in the granulator under conditions wherein the air temperature was 80° C. and the air flow rate was 50 m$^3$/hr, while spraying the aqueous solution of fasudil hydrochloride into the fluid-bed of NONPAREIL 105 under conditions wherein the spraying rate was 2 ml/min and the air pressure for spraying was 2 kg/cm$^2$ so as to coat the NONPAREIL 105 with fasudil hydrochloride, thereby obtaining 710 g of core member particles each having a particle diameter of from 600 µm to 850 µm. The same procedure as mentioned above was conducted thrice in total, so that 3 lots of the core members having a total weight of approximately 2,000 g were obtained.

REFERENCE EXAMPLE 2

The preparation of core member particles was conducted in substantially the same manner as in Reference Example 1 except that 400 g of fasudil hydrochloride hemihydrate was used instead of 400 g of fasudil hydrochloride anhydride and 350 g of CELPHERE CP-507 was used instead of 350 g of NONPAREIL 105, thereby obtaining 700 g of core member particles each having a particle diameter of from 600 µm to 850 µm. The same procedure as mentioned above was conducted thrice in total, so that 3 lots of the core members having a total weight of approximately 2,000 g were obtained.

REFERENCE EXAMPLE 3

1,400 g of fasudil hydrochloride hemihydrate and 70 g of HPC-L were dissolved in 2,100 ml of purified water to obtain an aqueous solution of fasudil hydrochloride. Using the obtained aqueous solution of fasudil hydrochloride, 700 g of CELPHERE CP-507 was subjected to coating with fasudil hydrochloride in the following manner. That is, 700 g of CELPHERE CP-507 was charged into an MP-01 model rolling fluid-bed granulator (manufactured and sold by POWREX CORPORATION, Japan), which was equipped with a sprayer. The aqueous solution of fasudil hydrochloride was charged in the sprayer of the granulator. The CELPHERE CP-507 was subjected to fluidization in the granulator under conditions wherein the air temperature was 85° C., the air flow rate was 70 m$^3$/hr and the revolution rate of the rotor was 400 rpm, while spraying the aqueous solution of fasudil hydrochloride into the fluid-bed of CELPHERE CP-507 under conditions wherein the spraying rate was 8 g/min and the air pressure for spraying was 0.3 MPa/cm$^2$ so as to coat the CELPHERE CP-507 with fasudil hydrochloride, thereby obtaining 2,155 g of core member particles each having a particle diameter of from 710 μm to 1,000 μm.

EXAMPLE 1

12 g of ethylcellulose was dissolved in 300 ml of ethanol to thereby obtain a solution. 36 g of talc was dispersed in the obtained solution to thereby prepare a coating dispersion. Using the obtained coating dispersion, 200 g of the core member produced in Reference Example 1 was subjected to coating with ethylcellulose and talc by the Wurster method in the following manner. That is, 200 g of the core member produced in Reference Example 1 was charged into a LAB-1 model fluid-bed granulator (manufactured and sold by POWREX CORPORATION, Japan), which was equipped with a sprayer. The coating dispersion was charged in the sprayer of the granulator. The core member produced in Reference Example 1 was subjected to fluidization in the granulator under conditions wherein the air temperature was 50° C. and the air flow rate was 50 m$^3$/hr, while spraying the coating dispersion into the fluid-bed of the core member under conditions wherein the spraying rate was 5 ml/min and the air pressure for spraying was 2 kg/cm$^2$ so as to coat the core member with ethylcellulose and talc, thereby obtaining sustained-release coated particles each having a particle diameter of from 600 to 1,000 μm. The obtained sustained-release coated particles were filled into No. 3 capsules in an amount of 185 mg per capsule, to thereby obtain an oral sustained-release preparation containing 80 mg of fasudil hydrochloride (in terms of the weight of fasudil hydrochloride anhydride).

EXAMPLE 2

The preparation of sustained-release coated particles was conducted in substantially the same manner as in Example 1 except that the core member produced in Reference Example 2 was used instead of the core member produced in Reference Example 1 and the amount of talc was changed to 60 g, thereby obtaining sustained-release coated particles each having a particle diameter of from 600 μm to 1,000 μm. The obtained sustained-release coated particles were filled into No. 2 capsules in an amount of 215 mg per capsule, to thereby obtain an oral sustained-release preparation containing 80 mg of fasudil hydrochloride (in terms of the weight of fasudil hydrochloride hemihydrate).

EXAMPLE 3

The preparation of sustained-release coated particles was conducted in substantially the same manner as in Example 2 except that the amount of the core member produced in Reference Example 2 was changed to 130 g, the amount of ethylcellulose was changed to 8 g, the amount of talc was change to 24 g, the air flow rate for fluidizing the core member was changed to 40 m$^3$/hr and the spraying rate of the coating dispersion was changed to 4 ml/min, thereby obtaining sustained-release coated particles each having a particle diameter of from 600 μm to 1,000 μm. The obtained sustained-release coated particles were filled into No. 3 capsules in an amount of 200 mg per capsule, to thereby obtain an oral sustained-release preparation containing 80 mg of fasudil hydrochloride (in terms of the weight of fasudil hydrochloride hemihydrate).

EXAMPLE 4

The preparation of sustained-release coated particles was conducted in substantially the same manner as in Example 1 except that the following conditions were used. 14.3 g of Eudragit RSPO was dissolved in 125 ml of ethanol to thereby obtain a solution. 42.9 g of talc was dispersed in the obtained solution to thereby prepare a coating dispersion. The thus prepared coating dispersion was used instead of the coating dispersion used in Example 1. In addition, the core member produced in Reference Example 1 was used in an amount of 190 g, instead of 200 g used in Example 1. By the above procedure, sustained-release coated particles each having a particle diameter of from 600 μm to 1,000 μm were obtained. The obtained sustained-release coated particles were filled into No. 3 capsules in an amount of 194 mg per capsule, to thereby obtain an oral sustained-release preparation containing 80 mg of fasudil hydrochloride (in terms of the weight of fasudil hydrochloride anhydride).

EXAMPLE 5

The preparation of sustained-release coated particles was conducted in substantially the same manner as in Example 1 except that 11.4 g of magnesium stearate was used instead of talc, the amount of ethylcellulose was changed to 11.4 g, the volume of ethanol was changed to 285 ml and the amount of the core member produced in Reference Example 1 was changed to 190 g, thereby obtaining sustained-release coated particles each having a particle diameter of from 600 μm to 1,000 μm. The obtained sustained-release coated particles were filled into No. 3 capsules in an amount of 167 mg per capsule, to thereby obtain an oral sustained-release preparation containing 80 mg of fasudil hydrochloride (in terms of the weight of fasudil hydrochloride anhydride).

EXAMPLE 6

Substantially the same procedure for producing sustained-release coated particles as in Example 2 was repeated except that the following conditions were used. 33 g of triethyl citrate and 100 g of magnesium stearate were added to 333 g of Aquacoat, and the resultant mixture was diluted with 350 ml of distilled water to thereby prepare a coating dispersion. The thus prepared coating dispersion was used instead of the coating dispersion used in Example 2. In addition, the air temperature in the granulator was 70° C. (instead of 50° C. used in Example 2) and the spraying rate of the coating dispersion was 2 ml/min (instead of 5 ml/min used in Example 2). By the above procedure, spraycoated particles were obtained. The obtained spraycoated particles were dried at 80° C. for 12 hrs to thereby obtain sustained-release coated particles each having a particle diameter of from 710 μm to 1,180 μm. The obtained sustained-release coated particles were filled into No. 1 capsules in an amount of 340 mg per capsule, to thereby obtain an oral sustained-release preparation containing 80 mg of fasudil hydrochloride (in terms of the weight of fasudil hydrochloride hemihydrate).

EXAMPLE 7

The preparation of sustained-release coated particles was conducted in substantially the same manner as in Example 1 except that the following conditions were used. 1.5 g of Eudragit RLPO and 13.5 g of Eudragit RSPO were dissolved in 250 ml of ethanol to thereby obtain a solution. 45 g of talc was dispersed in the obtained solution to thereby prepare a coating dispersion. The thus prepared coating dispersion was used instead of the coating dispersion used in Example 1. By the above procedure, sustained-release coated particles each having a particle diameter of from 600 μm to 1,000 μm were obtained. The obtained sustained-release coated particles were filled into No. 3 capsules in an amount of 194 mg per capsule, to thereby obtain an oral sustained-release preparation containing 80 mg of fasudil hydrochloride (in terms of the weight of fasudil hydrochloride anhydride).

EXAMPLE 8

Substantially the same procedure for producing sustained-release coated particles as in Example 2 was repeated except that the following conditions were used. 2 g of TC-5R was dissolved in 50 ml of a mixture of water and ethanol (the water/ethanol volume ratio was 1/1) to thereby obtain a solution. The thus obtained solution was used as a coating solution, instead of the coating dispersion used in Example 2. In addition, the spraying rate of the coating solution was 3 ml/min (instead of 5 ml/min used in Example 2). By the above procedure, coated particles A were obtained each having a particle diameter of from 600 μm to 850 μm and containing 50% by weight of fasudil hydrochloride (in terms of the weight of fasudil hydrochloride hemihydrate) (hereinafter, the coated particles A are referred to simply as "particles A").

On the other hand, the preparation of sustained-release coated particles was conducted in substantially the same manner as in Example 2 except that the following conditions were used. 2.25 g of Eudragit RLPO and 20.25 g of Eudragit RSPO were dissolved in 375 ml of ethanol to thereby obtain a solution. 67.5 g of talc was dispersed in the obtained solution to thereby prepare a coating dispersion. The thus prepared coating dispersion was used instead of the coating dispersion used in Example 2. By the above procedure, sustained-release coated particles B were obtained each having a particle diameter of from 600 μm to 1,000 μm and containing 35% by weight of fasudil hydrochloride (in terms of the weight of fasudil hydrochloride hemihydrate) (hereinafter, the sustained-release coated particles B are referred to simply as "particles B").

32 g of the above-obtained particles A and 183 g of the above-obtained particles B (wherein these weights correspond, respectively, to 2 parts by weight and 8 parts by weight in terms of the weight of fasudil hydrochloride hemihydrate) were uniformly mixed to thereby obtain mixed particles. 215 mg of the obtained mixed particles were filled into No. 2 capsules, to thereby obtain an oral sustained-release preparation containing 80 mg of fasudil hydrochloride (in terms of the weight of fasudil hydrochloride hemihydrate).

EXAMPLE 9

The preparation of sustained-release coated particles was conducted in substantially the same manner as in Example 2 except that 300 g of the core member produced in Reference Example 3 was used instead of the core member produced in Reference Example 2, the amount of ethylcellulose was changed to 18 g and the amount of talc was changed to 18 g, thereby obtaining sustained-release coated particles each having a particle diameter of from 850 μm to 1,180 μm. The obtained sustained-release coated particles were filled into No. 3 capsules in an amount of 14.3 mg per capsule, to thereby obtain an oral sustained-release preparation containing 80 mg of fasudil hydrochloride (in terms of the weight of fasudil hydrochloride hemihydrate).

EXAMPLE 10

18 g of ethylcellulose was dissolved in 306 ml of ethanol to thereby obtain a solution. 90 g of talc was dispersed in the obtained solution to thereby prepare a coating dispersion. Using the obtained coating dispersion, 400 g of the core member produced in Reference Example 3 was subjected to coating with ethylcellulose and talc in the following manner. That is, 400 g of the core member produced in Reference Example 3 was charged into an SFC-MINI model rolling fluid-bed granulator (manufactured and sold by Freund Industrial Co., Ltd., Japan), which was equipped with a sprayer. The coating dispersion was charged in the sprayer of the granulator. The core member produced in Reference Example 3 was subjected to fluidization in the granulator under conditions wherein the air temperature was 40° C., the fluidization air flow rate was 0.3 m$^3$/min, the slit air flow was 0.3 m$^3$/min and the revolution rate of the rotor was 800 rpm, while spraying the coating dispersion into the fluid-bed of the core member under condition wherein the spraying rate was 8 ml/min and the air pressure for spraying was 2 kg/cm$^2$ so as to coat the core member with ethylcellulose and talc, thereby obtaining sustained-release coated particles each having a particle diameter of from 850 to 1,180 μm. The obtained sustained-release coated particles were filled into No. 3 capsules in an amount of 158 mg per capsule, to thereby obtain an oral sustained-release preparation containing 80 mg of fasudil hydrochloride (in terms of the weight of fasudil hydrochloride anhydride).

EXAMPLE 11

The preparation of sustained-release coated particles was conducted in substantially the same manner as in Example 10 except that the amount of ethylcellulose was changed to 20 g, the amount of talc was changed to 100 g and the volume of ethanol was changed to 340 ml, thereby obtaining sustained-release coated particles each having a particle diameter of from 850 μm to 1,180 μm. The obtained sustained-release coated particles as such were packed, as a granular oral sustained-release preparation, in packages in an amount of 163 mg per package. The oral sustained-release preparation contained 80 mg of fasudil hydrochloride (in terms of the per-package weight of fasudil hydrochloride hemihydrate)

COMPARATIVE EXAMPLE 1

Substantially the same procedure for producing sustained-release coated particles as in Example 1 was repeated except that talc was not used, thereby obtaining coated particles each having a particle diameter of from 600 μm to 1,000 μm. The obtained coated particles were filled into No. 2 capsules in an amount of 200 mg per capsule, to thereby obtain an oral capsule preparation containing fasudil hydrochloride.

COMPARATIVE EXAMPLE 2

Substantially the same procedure for producing sustained-release coated particles as in Example 2 was repeated except that a coating solution obtained by dissolving 3 g of Eudragit RLPO and 27 g of Eudragit RSPO in 500 ml of ethanol was used instead of the coating dispersion used in Example 2, thereby obtaining coated particles each having a particle diameter of from 600 μm to 1,000 μm. The obtained coated particles were filled into No. 2 capsules in an amount of 200 mg per capsule, to thereby obtain an oral capsule preparation containing fasudil hydrochloride.

COMPARATIVE EXAMPLE 3

Substantially the same procedure for producing sustained-release coated particles as in Example 6 was repeated except that magnesium stearate was not used, the amount of triethyl citrate was changed to 33.5 g and the volume of distilled water was changed to 300 ml, thereby obtaining coated particles each having a particle diameter of from 600 μm to 1,000 μm. The obtained coated particles were filled into No. 2 capsules in an amount of 200 mg per capsule, to thereby obtain an oral capsule preparation containing fasudil hydrochloride.

COMPARATIVE EXAMPLE 4

Substantially the same procedure for producing the sustained-release coated particles as in Example 4 was repeated except that a dispersion obtained by dispersing 172.5 g of talc in a solution obtained by dissolving 11.5 g of Eudragit RSPO in 400 ml of ethanol was used as the coating dispersion, thereby obtaining coated particles each having a particle diameter of from 600 to 1,000 μm. The obtained coated particles were filled into No. 2 capsules in an amount of 200 mg per capsule, to thereby obtain an oral capsule preparation containing fasudil hydrochloride.

COMPARATIVE EXAMPLE 5

80 g of fasudil hydrochloride anhydride, 360 g of D-mannitol, 28 g of NS-300, 12 g of HPC-L, 120 g of AVICEL PH301, 4 g of ADOSOLIDER 101 and 3.2 g of magnesium stearate were mixed with each other and then, compression-molded by means of a dry granulator Roller Compactor Mini (manufactured and sold by Freund Industrial Co., Ltd., Japan) to thereby obtain granules. The obtained granules were sieved to thereby collect granules having a predetermined size. The collected granules were mixed with 4.8 g of magnesium stearate and the resultant granules for tableting were charged into a CP-12 model rotary tableting machine (manufactured and sold by Kikusui Seisakusho Ltd., Japan) and subjected to tableting to thereby obtain uncoated tablets each having a weight of 153 mg.

19.6 g of TC-5RW and 2.8 g of ethylcellulose were dissolved in 375 ml of a mixture of purified water and ethanol (purified water:ethanol=1:4 (volume ratio)) to thereby obtain a solution. Then, 5.6 g of titanium oxide (anatase type) was dispersed in the obtained solution, thereby obtaining a coating dispersion. Using the obtained coating dispersion, the above-obtained uncoated tablets were subjected to coating in the following manner. That is, the uncoated tablets were charged into a DRC-300 model coating machine (manufactured and sold by POWREX CORPORATION, Japan) which was equipped with a sprayer. The coating dispersion was charged into the sprayer of the coating machine. The above-obtained uncoated tablets were subjected to fluidization in the coating machine under conditions wherein the air temperature was 80° C. and the air flow rate was 1.2 m$^3$/min, while spraying the coating dispersion into the fluid-bed of the uncoated tablets so as to coat the uncoated tablets, thereby obtaining coated tablets.

Subsequently, the obtained coated tablets are subjected to polishing treatment in the coating machine in the following manner. Approximately 0.13 g of Polishing WAX 103 was charged into the coating machine, and the rolling of the tablets was conducted in the coating machine for 30 minutes while feeding heated air (temperature: 60° C.) into the coating machine. Then, the feeding of heated air was stopped, but the rolling of the tablets was continued for further 30 minutes, thereby obtaining tablet preparations each having a weight of 160 mg.

Further, substantially the same procedure as described above was repeated except that fasudil hydrochloride hemihydrate was used in an amount of 82.2 g (that is, 80 g in terms of the weight of fasudil hydrochloride anhydride) instead of fasudil hydrochloride anhydride, thereby obtaining tablet preparations each having a weight of 160.6 mg.

COMPARATIVE EXAMPLE 6

822 g of fasudil hydrochloride hemihydrate, 3078 g of D-mannitol and 1,000 g of corn starch were charged into an FLO-15 model fluid-bed granulator equipped with a sprayer (manufactured and sold by Freund Industrial Co., Ltd., Japan) and then, subjected to fluidization in the granulator, while spraying (by the top spraying method) an aqueous solution of HPC-L (obtained by dissolving 120 g of HPC-L in 2480 g of purified water) into the fluid-bed in the sprayer, thereby obtaining granules. The obtained granules were dried in the granulator. The obtained dried granules were mixed with 120 g of Primojel (as a disintegrant) and 60 g of magnesium stearate (as a lubricant) to thereby obtain granules for tableting. The obtained granules for tableting were charged into a CP-12 model rotary tableting machine (manufactured and sold by Kikusui Seisakusho Ltd., Japan) and subjected to tableting to thereby obtain uncoated tablets each having a weight of 130 mg.

220 g of TC-5RW was dissolved in 3600 ml of purified water to thereby obtain a solution, and 60 g of titanium oxide was dispersed in the obtained solution, thereby obtaining a coating dispersion. Using the coating dispersion, the above-obtained uncoated tablets were subjected to coating in the following manner. That is, the uncoated tablets were charged into a DRC-650 model coating machine (manufactured and sold by POWREX CORPORATION, Japan) which was equipped with a sprayer. The coating dispersion was charged into the sprayer of the coating machine.

The above-obtained uncoated tablets were subjected to fluidization in the coating machine under conditions wherein the air temperature was 80° C. and the air flow rate was 6 m$^3$/min, while spraying the coating dispersion into the fluid-bed of the uncoated tablets so as to coat the uncoated tablets, thereby obtaining coated tablets.

Subsequently, the obtained coated tablets were subjected to polishing treatment in the coating machine in the following manner. Approximately 1.3 g of Polishing WAX 103 was charged into the coating machine, and the rolling of the tablets in the coating machine was conducted in the coating machine for 30 minutes while feeding heated air (temperature: 60° C.) into the coating machine. Then, the feeding of heated air was stopped, but the rolling of the tablets was continued for further 30 minutes, thereby obtaining tablet preparations each having a weight of 137 mg.

Further, substantially the same procedure as described above was repeated except that 800 g of fasudil hydrochloride anhydride was used instead of fasudil hydrochloride hemihydrate, thereby obtaining tablet preparations each having a weight of 136.5 mg.

EXPERIMENT 1

The oral sustained-release preparations produced in Examples 1 to 11, the oral capsule preparations produced in Comparative Examples 1 to 4 and the tablet preparations produced in Comparative Examples 5 and 6 were each subjected to the dissolution test in accordance with method 2 (paddle method) of the dissolution test described in the Japanese Pharmacopoeia Thirteenth Edition for measuring a dissolution rate of an active ingredient from the preparation. The method for the test is explained below. In the explanation made below, the amount of the active ingredient is defined as the weight of fasudil hydrochloride anhydride. That is, as mentioned above, when a fasudil hydrochloride hydrate is used as the active ingredient, the weight of an equimolar amount of fasudil hydrochloride anhydride is taken as the amount of the active ingredient.

A DT-610 model dissolution test apparatus (which is manufactured and sold by Japan Spectroscopic Co., Ltd., Japan and is in conformity with the Japanese Pharmacopoeia) was used for the dissolution test.

Distilled water (deaerated by ultrasonication under reduced pressure (using an aspirator) for 10 minutes) was used as a dissolution medium.

First, 900 ml of the dissolution medium was added to a vessel of the dissolution test apparatus, and the temperature of the dissolution medium was maintained at 37±0.5° C.

Next, a paddle was attached to the apparatus, and a sample of the above-mentioned preparation was placed in the sinker and allowed to sink to the center of the bottom of the vessel (with respect to the oral sustained-release preparation produced in Example 11, 163 mg (corresponding to one dose) of the preparation was allowed to directly sink to the center of the bottom of the vessel without using the sinker). The revolution of the paddle was started immediately after the sample reached the bottom of the vessel. The revolution rate of the paddle was adjusted to 100±4 revolutions per minute. During the subsequent steps, the opening of the vessel was covered to prevent the evaporation of the dissolution medium.

At the points in time of 1, 2, 3, 4, 6, 8, 10, 12, 15 and 20 hours after the start of the dissolution test (namely, after the start of the revolution of the paddle), 10 ml of the dissolution medium containing the active ingredient released from the preparation (hereinafter referred to as an "active ingredient-dissolved solutions") was collected from the vessel at a position which is intermediate between the surface of the dissolution medium and the top of the paddle, and 10 mm distant from the inner wall of the vessel. Immediately after collecting the active ingredient-dissolved solution, 10 ml of distilled water heated to 37±0.5° C. was carefully added to the vessel to thereby compensate for the dissolution medium taken from the vessel. The collected active ingredient-dissolved solution was filtered using a membrane filter (Omunipore membrane Milex LH (diameter: 25 mm, pore size: 0.5 μm); manufactured and sold by Japan Milipore Co., Ltd., Japan) and the resultant filtrate was used as a sample solution.

The sample solutions prepared from the active ingredient-dissolved solutions respectively collected at the points in time of 1, 2, 3, 4, 6, 8, 10, 12, 15 and 20 hours after the start of the dissolution test are referred to as "the 1st, 2nd, . . . and 10th sample solution", respectively.

Apart from the above operation, a standard fasudil hydrochloride solution was prepared by dissolving a 80 mg of a standard fasudil hydrochloride (which had been weighed precisely) in distilled water, followed by adjusting the volume of the aqueous fasudil hydrochloride solution to 1,000 ml. With respect to the sample solution and the standard fasudil hydrochloride solution, an absorbance at 275 nm (hereinafter referred to simply as the "absorbance") was measured.

The dissolution rate (%) of the active ingredient at the point in time of collecting the 1st sample solution, that is, at the point in time of 1 hour after the start of the dissolution test, based on the weight of the active ingredient originally contained in the preparation (hereinafter, referred to simply as a "dissolution rate"), was calculated by the following formula:

Dissolution rate (%) at the point in time of collecting the 1st sample solution=$100\times\{m_s \times A_1 \div (A_s \times 1000 \div 900) \div m_t\}$ wherein:

$m_t$: total weight of the active ingredient originally contained in the preparation;

$m_s$: weight of the active ingredient used for preparing the standard solution;

$A_1$: absorbance of the 1st sample solution; and $A_s$: absorbance of the standard solution.

Further, the dissolution rate (%) at the point in time of collecting the i-th (i represents an integer of from 2 to 10) sample solution, that is, at the point in time of $t_i$ hours after the start of the dissolution test, based on the weight of the active ingredient originally contained in the preparation, was calculated by the following formula:

Dissolution rate at the point in time of $t_i$ hours from the start of the dissolution test (%) =

$$100 \times \left\{ m_s \times \left( A_i + \sum_{j=1}^{i-1} A_j \times 10 \div 900 \right) \div (A_s \times 1000 \div 900) \div m_t \right\}$$

wherein:

$m_t$: total weight of the active ingredient originally contained in the preparation;

$m_s$: weight of the active ingredient used for preparing the standard solution;

$A_i$: absorbance of the i-th sample-solution;

$A_s$: absorbance of the standard solution; and $\sum_{j=1}^{i-1} A_j$: sum of the absorbances of the 1st to (i−1)-th sample solutions.

The above-mentioned test was repeated six times and the mean of the dissolution rates obtained at the point in time of i hours after the start of the dissolution test was determined.

The results are shown in Table 1.

TABLE 1

| Preparation | Coating base material:insoluble auxiliary material* | Dissolution Rate (%) | | | |
|---|---|---|---|---|---|
| | | 1 hr | 3 hrs | 6 hrs | 15 hrs |
| Example 1 | 1:3 | 6 | 34 | 59 | 94 |
| Example 2 | 1:5 | 3 | 21 | 49 | 88 |
| Example 3 | 1:3 | 3 | 34 | 64 | 93 |
| Example 4 | 1:3 | 4 | 7 | 36 | 93 |
| Example 5 | 1:1 | 3 | 22 | 49 | 82 |
| Example 6 | 1:3 | 0 | 27 | 58 | 90 |
| Example 7 | 1:3 | 5 | 11 | 42 | 97 |
| Example 8 | 1:3** | 20 | 23 | 37 | 72 |
| Example 9 | 1:1 | 4 | 22 | 50 | 89 |
| Example 10 | 1:5 | 5 | 22 | 52 | 96 |
| Example 11 | 1:5 | 3 | 17 | 45 | 90 |

TABLE 1-continued

| Preparation | Coating base material:insoluble auxiliary material* | Dissolution Rate (%) | | | |
|---|---|---|---|---|---|
| | | 1 hr | 3 hrs | 6 hrs | 15 hrs |
| Comparative Example 1 | 1:0 | 50 | 82 | 90 | 98 |
| Comparative Example 2 | 1:0 | 83 | 93 | 94 | 95 |
| Comparative Example 3 | 1:0 | 13 | 63 | 81 | 96 |
| Comparative Example 4 | 1:15 | 1 | 5 | 25 | 53 |
| Comparative Example 5 | None*** | 100 | — | — | — |
| Comparative Example 6 | None*** | 100 | — | — | — |

*The weight ratio of insoluble auxiliary material in each coating of the sustained-release particles was given on the assumption that the weight of the coating base material is 1.
**The ratio of insoluble auxiliary material in B particles is shown, since A particles do not contain the insoluble auxiliary material.
***Preparations of Comparative Examples 5 and 6 do not contain sustained-release particles although each of preparations of Comparative Examples 5 and 6 is a tablet coated with a layer containing an insoluble auxiliary material.

As shown in Table 1, with respect to each of the sustained-release preparations of the present invention, produced in Examples 1 to 11 (each of which contains the sustained-release coated particle having a coating containing the insoluble auxiliary material), the amounts of the active ingredient released from the preparation at the points in time of 3, 6 and 15 hours after the start of the test were 5 to 35% by weight, 35 to 65% by weight, and 70% by weight or more, respectively.

On the other hand, with respect to each of the capsule preparations produced in Comparative Examples 1 to 3 (each of which contains the coated particle having a coating which does not contain the insoluble auxiliary material.), 50% by weight or more of the active ingredient was quickly released from the preparation within 3 hours after the start of the test.

With respect to the capsule preparation produced in Comparative Example 4, although the preparation contained coated particles having a coating containing the insoluble auxiliary material, the release of the active ingredient was extremely slow. The reason for such slow release is considered to be that the amount of the insoluble auxiliary material contained in the coating was too large.

Further, each of the preparations produced in Comparative Examples 5 and 6 is a tablet coated with a layer containing the insoluble auxiliary material; however, each of the preparations does not contain the sustained-release coated particle. As in the case of the capsule preparations of Comparative Examples 1 to 3, in Comparative Examples 5 and 6, the active ingredient was quickly released from each of the preparations within 3 hours after the start of the test.

From the above, it is apparent that, for controlling the release of an active ingredient from a preparation containing fasudil hydrochloride or a hydrate thereof as the active ingredient, it is necessary that the preparation contain the sustained-release coated particle having the coating containing an insoluble auxiliary material.

EXPERIMENT 2

In order to evaluate the oral sustained-release preparation of the present invention with respect to the sustained-release ability of the active ingredient in the lower portion of the digestive tract (in which the amount of the internal liquid of the digestive tract is small), a dissolution test was conducted using a dissolution medium only in a small amount. The method of this dissolution test is explained below. In the explanation made below, the amount of the active ingredient is defined as the weight of fasudil hydrochloride anhydride. That is, as mentioned above, when a fasudil hydrochloride hydrate is used as the active ingredient, the weight of an equimolar amount of fasudil hydrochloride anhydride is taken as the amount of the active ingredient.

As a dissolution test apparatus, an apparatus comprising a reservoir, a constant flow pump and a cell (each of which is described below) was used, wherein the reservoir, constant flow pump and cell were connected in this order so that a dissolution medium in the reservoir was introduced into the cell by means of the constant flow pump.

Reservoir: Terumo Syringe SS-10S (internal volume: 10 ml; manufactured and sold by Terumo Corp., Japan)

Constant flow pump: 230P model pump (which is capable of transferring a liquid at an extremely low flow rate) (manufactured and sold by KD Scientific Inc., U.S.A.) (hereinafter referred to simply as the "pump")

Cell: The cylinder part of Terumo Syringe SS-01P (internal volume: 1 ml) (manufactured and sold by Terumo Corp., Japan) was cut to thereby obtain a cylinder having a length of 23 mm. A gasket (specifically, a rubber packing fitted on the forward end of the piston of the above-mentioned syringe) was inserted into each end of the obtained cylinder so that the distance between the two gaskets became 15.5 mm, to thereby form a space (between the gaskets) having a volume of approximately 0.5 ml. The thus obtained cylinder having two gaskets inserted into both ends was used as the cell.

With respect to each of the above-mentioned gaskets, a through-hole was formed at the center thereof, and two silicone tubes for liquid transfer (length: 10 cm, inner diameter: 1 mm, outer diameter: 3 mm) were, respectively, inserted into the cylinder through the through-holes of the gaskets.

One of these two silicone tubes was connected to the pump, so that the dissolution medium was able to be introduced into the cell by means of the pump through one silicone tube, and the introduced dissolution medium was able to be discharged from the cell through the other silicone tube which was not connected to the pump. Hereinafter, the expression "discharged from the cell" means being "discharged from the cell through the silicone tube which was not connected to the pump".

The thus obtained dissolution test apparatus was placed in a constant temperature room in which the room temperature was 37±0.5° C. The dissolution test was conducted in accordance with method 3 (flow-through cell method) of the dissolution test described in the Japanese Pharmacopoeia Thirteenth Edition.

Two circular filter papers (each having a diameter of 6 mm) and 183 mg of the sustained-release coated particles (before being filled in a capsule) produced in Example 2 were placed in the cell of the dissolution test apparatus so that the particles were placed between the two filter papers. The circular filter papers were used for preventing the particles from flowing out of the cell.

A dissolution medium (distilled water, 37° C.) was placed in the reservoir, and transferred to and introduced into the cell (containing the sustained-release coated particles of the present invention) by means of the pump at a flow rate of 0.4 ml/hr. During the period of from the start of the introduction of the dissolution medium to the point in time of 1 hour after the start of the introduction of the dissolution medium, the resultant solution, containing the active ingredient released from the preparation (hereinafter referred to as the "active ingredient-dissolved solution"), discharged from the cell was collected in a 10 ml flask (that is, a 1-hour sampling was conducted). The same 1-hour sampling of the active ingredient-dissolved solution as mentioned above was successively conducted 20 times in total. Each of the 20 active ingredientdissolved solutions respectively obtained in small amounts as obtained using 0.4 ml/hr-of dissolution medium by the 20-time 1-hour sampling was diluted to 10 ml, and each of the resultant diluted, active ingredient-dissolved solutions was further diluted 100-fold, thereby obtaining 20 sample solutions.

Hereinafter, a sample solution prepared from the active ingredient-dissolved solution collected during the period of from the point in time of (i−1) hour(s) after the start of the dissolution test to the point in time of i hours after the start of the dissolution test (wherein i represents an integer of from 1 to 20) is referred to as the "i-th sample solution".

80 mg of standard fasudil hydrochloride was accurately weighed and dissolved in distilled water so that the resultant solution had a volume of 100 ml. 1 ml of the obtained solution was diluted 100-fold, thereby obtaining a standard solution of fasudil hydrochloride. With respect to each of the sample solutions and the standard solution, the absorbance at a wavelength of 275 nm (hereinafter referred to simply as the "absorbance") was measured.

The weight percent (%) of the dissolved active ingredient at the end of the 1-hour sampling for obtaining the active ingredient-dissolved solution used for preparing the i-th sample solution, based on the weight of the active ingredient originally contained in the preparation (hereinafter referred to simply as the "dissolution rate") was calculated by the following formula.

Dissolution rate (weight %) at the end of the 1-hour sampling for obtaining the active ingredient-dissolved solution used for preparing $$\text{the } i\text{-th sample solution} = 100 \times \left\{ \left( m_s \times \sum_{j=1}^{i} A_j \right) \div (A_s \times 10) \right\} \div m_t$$

wherein the meanings of the characters are as follows:

$m_t$: the total weight of the active ingredient originally contained in the preparation;

$m_s$: the weight of the active ingredient used for preparing the standard solution;

$A_s$: the absorbance of the standard solution; and $\sum_{j=1}^{i} A_j$: the sum of the absorbances of the 1st to $i$-th sample solutions.

The results of the calculation are shown in Table 2 (see the item "Dissolution test using a small amount of dissolution medium").

For comparison, Table 2 also shows the results of the dissolution test (see Experiment 1) in which the sustained-release capsule preparation produced in Example 2 was subjected to a testing according to the paddle method (see the item "Paddle method").

TABLE 2

|  | Dissolution rate (% by weight) | | | | | | |
| --- | --- | --- | --- | --- | --- | --- | --- |
|  | 1 hr | 2 hrs | 3 hrs | 4 hrs | 6 hrs | 8 hrs | 20 hrs |
| Dissolution test using a small amount of dissolution medium | 1 | 10 | 21 | 30 | 51 | 66 | 97 |
| Paddle method | 3 | 11 | 21 | 31 | 49 | 64 | 97 |

Table 2 shows that, under conditions wherein only a small amount of the dissolution medium is used, the active ingredient of the oral sustained-release preparation of the present invention exhibits a sustained-release ability which is about the same as that exhibited under conditions wherein a large amount (900 ml) of the dissolution medium is present.

This means that a satisfactory amount of the active ingredient is released from the oral sustained-release preparation of the present invention even in the lower portion of the digestive tract (in which the amount of the internal liquid of the digestive tract is small). Therefore, the results of the above experiment suggest that the oral sustained-release preparation of the present invention is advantageous.

EXPERIMENT 3

A minicapsule for rats (diameter: about 2 mm, length: about 8 mm) was filled with the sustained-released coated particles produced in Example 2 to thereby obtain a sustained-release capsule preparation for rats, wherein the sustained-release coated partidles were used in an amount corresponding to approximately 1.5 mg of fasudil hydrochloride anhydride.

The obtained capsule preparation and 0.5 ml of water were orally administered to rats which had previously been fasted. At predetermined points in time after the administration, blood samples were respectively taken from the rat and the concentration of the 1-hydroxy derivative of fasudil hydrochloride (hereinafter referred to simply as the "active metabolite") in each blood sample was measured by the above-mentioned HPLC method.

FIG. 1 shows the change (with the lapse of time) of the concentration of the active metabolite in the blood taken from the rat.

It is apparent from FIG. 1 that, when the oral sustained-release preparation produced in Example 2 was orally administered, the concentration of the active metabolite in the blood was maintained in a desired range for a long period of time.

EXPERIMENT 4

Substantially the same procedure as in Experiment 3 was repeated, except that the sustained-release coated particles produced in Example 3 were used instead of the sustained-release coated particles produced in Example 2.

Figure 2:
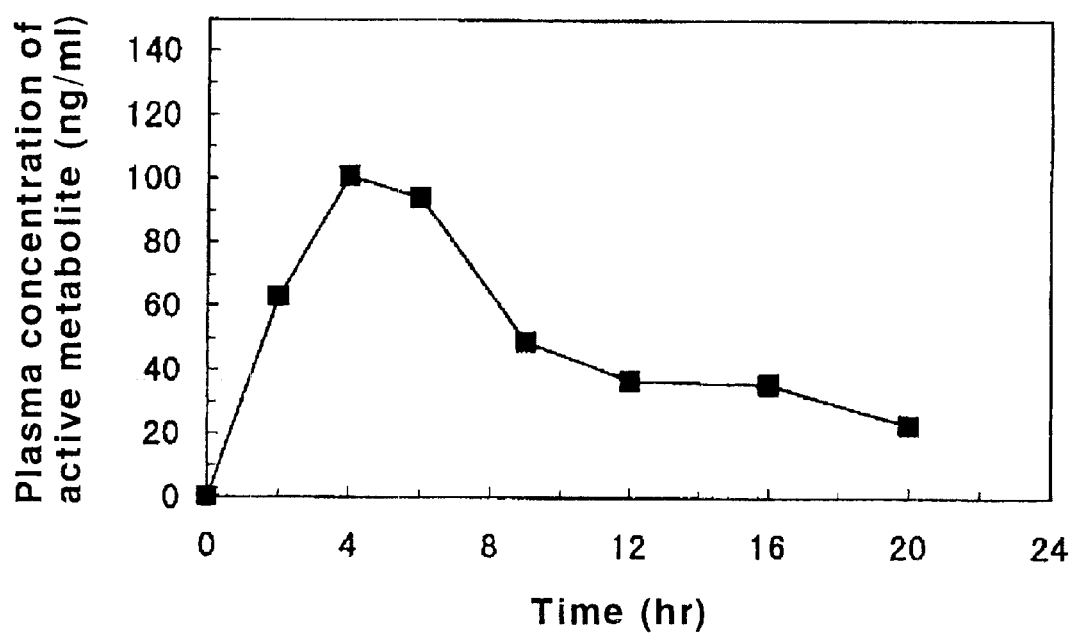
FIG. 2 is a graph showing the change (with the lapse of time) of the plasma concentration of the active metabolite in rats, which is obtained by orally administering the oral sustained-release preparation produced in Example 3.

FIG. 2 shows the change (with the lapse of time) of the concentration of the active metabolite in the blood taken from the rat.

It is apparent from FIG. 2 that, when the oral sustained-release preparation produced in Example 3 was orally administered, the concentration of the active metabolite in the blood was maintained in a desired range for a long period of time.

EXPERIMENT 5

Substantially the same procedure as in Experiment 3 was repeated, except that the sustained-release coated particles produced in Example 4 were used instead of the sustained-release coated particles produced in Example 2.

Figure 3:
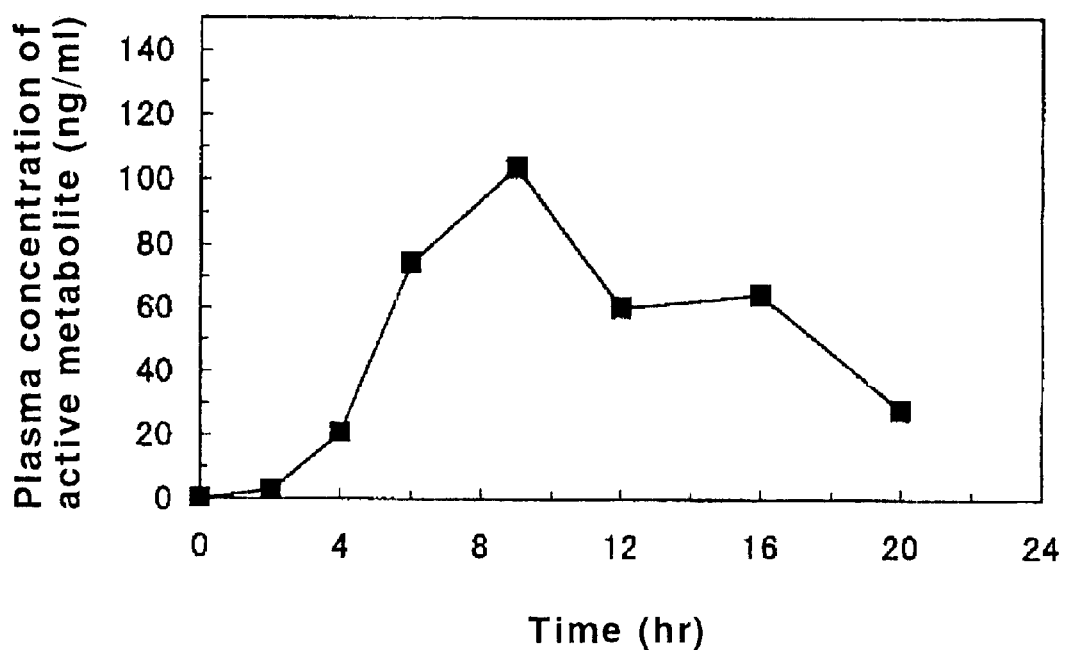
FIG. 3 is a graph showing the change (with the lapse of time) of the plasma concentration of the active metabolite in rats, which is obtained by orally administering the oral sustained-release preparation produced in Example 4.

FIG. 3 shows the change (with the lapse of time) of the concentration of the active metabolite in the blood taken from the rat.

It is apparent from FIG. 3 that, when the oral sustained-release preparation produced in Example 4 was orally administered, the concentration of the active metabolite in the blood was maintained in a desired range for a long period of time.

EXPERIMENT 6

Substantially the same procedure as in Experiment 3 was repeated, except that the sustained-release coated particles produced in Example 8 were used instead of the sustained-release coated particles produced in Example 2.

Figure 4:
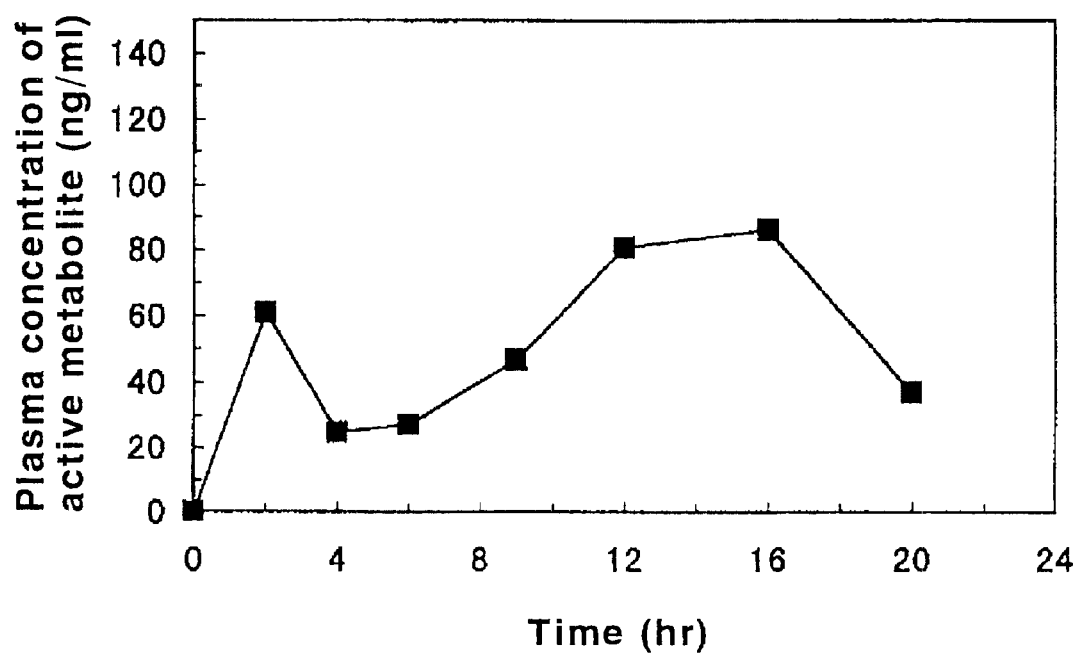
FIG. 4 is a graph showing the change (with the lapse of time) of the plasma concentration of the active metabolite in rats, which is obtained by orally administering the oral sustained-release preparation produced in Example 8.

FIG. 4 shows the change (with the lapse of time) of the concentration of the active metabolite in the blood taken from the rat.

It is apparent from FIG. 4 that, when the oral sustained-release preparation produced in Example 8 was orally administered, the concentration of the active metabolite in the blood was maintained in a desired range for a long period of time.

EXPERIMENT 7

Substantially the same procedure as in Experiment 3 was repeated, except that the sustained-release coated particles produced in Example 10 were used instead of the sustained-release coated particles produced in Example 2.

Figure 5:
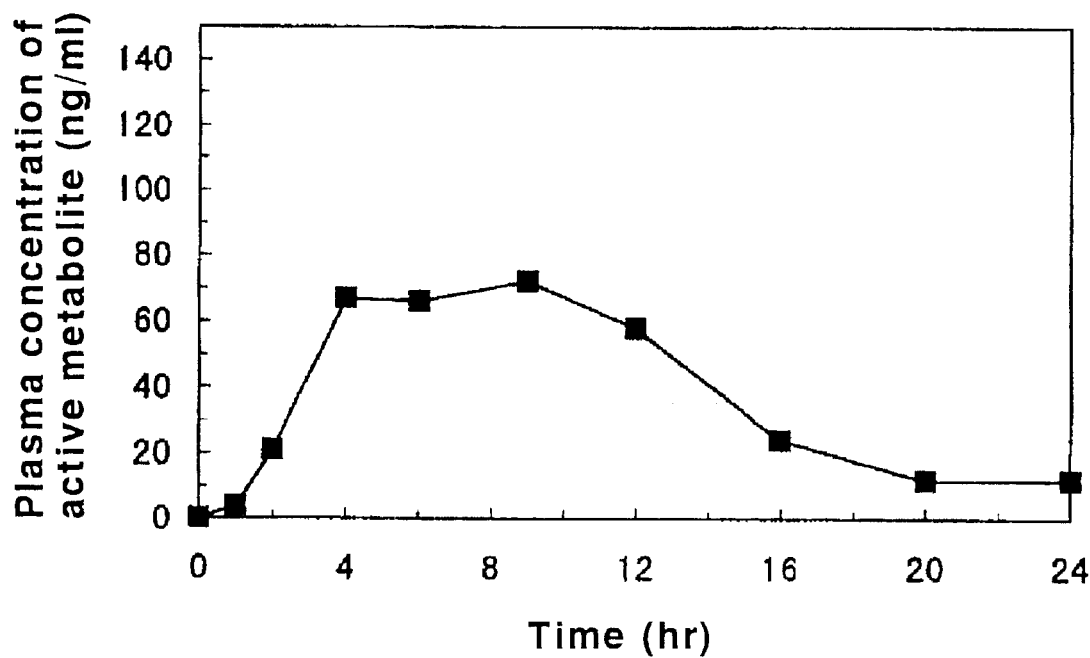
FIG. 5 is a graph showing the change (with the lapse of time) of the plasma concentration of the active metabolite in rats, which is obtained by orally administering the oral sustained-release preparation produced in Example 10.

FIG. 5 shows the change (with the lapse of time) of the concentration of the active metabolite in the blood taken from the rat.

It is apparent from FIG. 5 that, when the oral sustained-release preparation produced in Example 10 was orally administered, the concentration of the active metabolite in the blood was maintained in a desired range for a long period of time.

EXPERIMENT 8

Substantially the same procedure as in Experiment 3 was repeated, except that the coated particles produced in Comparative Example 3 were used instead of the sustained-release coated particles produced in Example 2.

Figure 6:
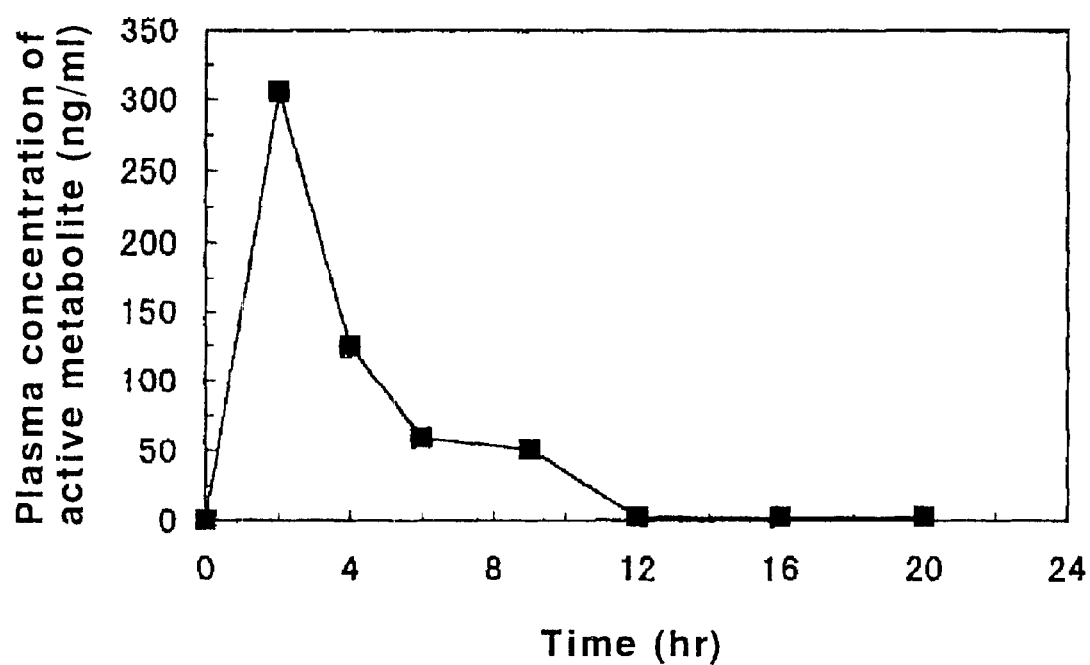
FIG. 6 is a graph showing the change (with the lapse of time) of the plasma concentration of the active metabolite in rats, which is obtained by orally administering the oral sustained-release preparation produced in Comparative Example 3.

FIG. 6 shows the change (with the lapse of time) of the concentration of the active metabolite in the blood taken from the rat.

It is apparent from FIG. 6 that, when the oral sustained-release preparation produced in Comparative Example 3 was orally administered, the concentration of the active metabolite in the blood rapidly, markedly increased and then rapidly, markedly decreased, so that it was impossible to maintain the concentration of the active metabolite in the blood in a desired range for a long period of time.

EXPERIMENT 9

Substantially the same procedure as in Experiment 3 was repeated, except that the coated particles produced in Comparative Example 4 were used instead of the sustained-release coated particles produced in Example 2.

Figure 7:
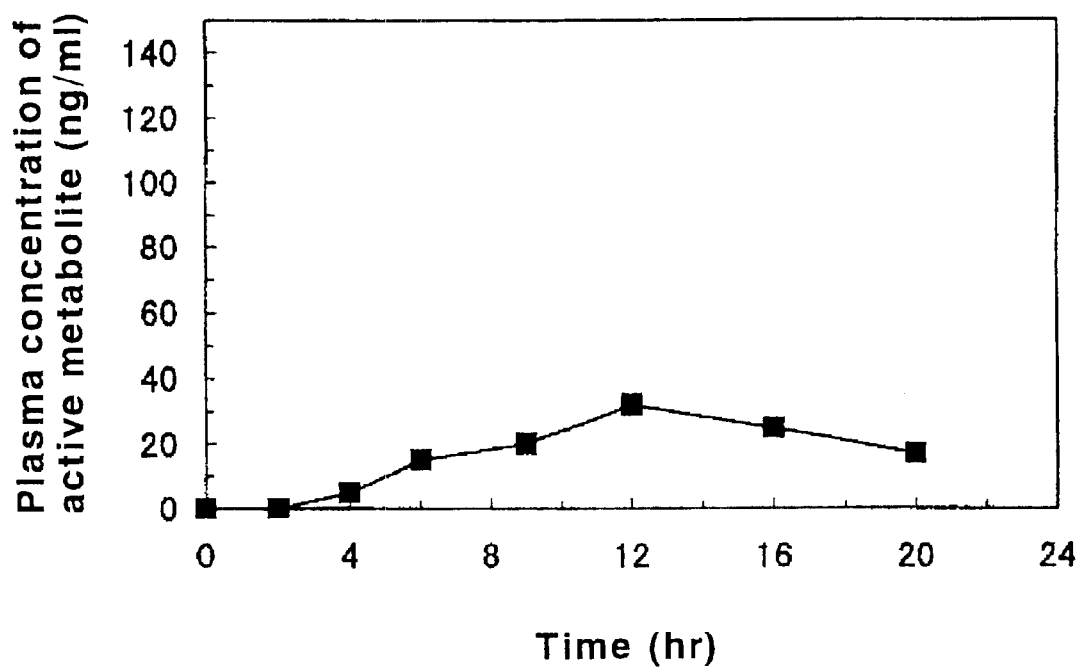
FIG. 7 is a graph showing the change (with the lapse of time) of the plasma concentration of the active metabolite in rats, which is obtained by orally administering the oral sustained-release preparation produced in Comparative Example 4.

FIG. 7 shows the change (with the lapse of time) of the concentration of the active metabolite in the blood taken from the rat.

It is apparent from FIG. 7 that, when the oral preparation produced in Comparative Example 4 was orally administered, the concentration of the active metabolite in the blood did not satisfactorily increase, so that it was impossible to maintain the concentration of the active metabolite in the blood in a desired range for a long period of time.

The results of Experiments 3 to 7 clearly show that, when the oral sustained-release preparation of the present invention was orally administered to rats, the concentration of the active metabolite in the blood was maintained in a desired range for a long period of time. The reason for this is considered to be as follows. When the oral sustained-release preparation of the present invention was orally administered, a desired amount of the active ingredient was continued to be released from the preparation over a long period of time, so that the released active ingredient was absorbed over the whole region of the digestive tract of the rat and metabolized to the active metabolite, and, in turn, the active metabolite was continued to be transferred to the circulating blood of the rat.

By contrast, with respect to the preparation of Comparative Example 3 (used in Experiment 8), the reason for the unsatisfactory results of Experiment 8 is considered to be as follows. When the oral preparation produced in Comparative Example 3 was orally administered, the active ingredient was rapidly released from the preparation, so that the concentration of the active metabolite in the blood rapidly increased. However, the release of the active ingredient was completed in a short period of time. Accordingly, the concentration of the active metabolite in the blood rapidly decreased, so that it was impossible to maintain the concentration in the blood in a desired range for a long period of time.

Further, with respect to the preparation of Comparative Example 4 (used in Experiment 9), the reason for the unsatisfactory results of Experiment 9 is considered to be as follows. When the oral preparation produced in Comparative Example 4 was orally administered, the active ingredient was released from the preparation at an extremely slow rate, so that the amount of the active ingredient released from the preparation was unsatisfactory and, hence, the amount of the active ingredient absorbed by the digestive tract was unsatisfactory. As a result, the concentration of the active metabolite in the blood did not satisfactorily increase.

From the above, it is apparent that, for maintaining the concentration of the fasudil hydrochloridederived active metabolite in the blood in a desired range for a long period of time, it is necessary that fasudil hydrochloride or a hydrate thereof be administered in the form of a preparation which exhibits the above-described desired dissolution rates with respect to the active ingredient, as measured by the above-described methods.

INDUSTRIAL APPLICABILITY

By using the oral sustained-release preparation of the present invention, it is possible to surely control the release of fasudil hydrochloride from the preparation, so that a desired amount of fasudil hydrochloride is continued to be released from the preparation for a long period of time, and that the effect of fasudil hydrochloride is maintained for a long period of time. Therefore, the frequency of the administration of the preparation becomes low, so that the burden of the patient who has to take the preparation can be decreased and the compliance with respect to the administration of the preparation can be improved. As a result, the therapeutic effect of fasudil hydrochloride is rendered reliable. Therefore, the oral sustained-release preparation of the present invention is extremely useful.

What is claimed is:

1. An oral sustained-release preparation containing fasudil hydrochloride as an active ingredient, wherein said fasudil hydrochloride is represented by the following formula:

said preparation comprising at least one sustained-release coated particle comprising a core having a surface and a coating formed on the surface of said core, wherein said core contains said active ingredient and said coating comprises a coating base material and an insoluble auxiliary material in the form of a fine powder or fine particles which are pharmaceutically acceptable and insoluble in water and ethanol, said preparation exhibiting, with respect to said active ingredient, the following dissolution rates (1), (2) and (3), as measured by a dissolution test apparatus in conformity with the Japanese Pharmacopoeia Thirteenth Edition under conditions wherein the amount of a dissolution medium is 900 ml, the temperature of the dissolution medium is 37±0.5° C., and the revolution rate of a paddle is 100±4 revolutions per minute:
  (1) dissolution of 5 to 40% by weight, based on the weight of said active ingredient originally contained in said preparation, at the point in time of 3 hours after the start of the dissolution test,
  (2) dissolution of 35 to 70% by weight, based on the weight of said active ingredient originally contained in said preparation, at the point in time of 6 hours after the start of the dissolution test, and
  (3) dissolution of 70% by weight or more, based on the weight of said active ingredient originally contained in said preparation, at the point in time of 15 hours after the start of the dissolution test.

2. The oral sustained-release preparation according to claim 1, wherein the amount of said active ingredient which is contained in said core is at least 30% by weight, based on the weight of said active ingredient contained in said preparation.

3. The oral sustained-release preparation according to claim 1, wherein the amount of said active ingredient which is contained in said core is substantially 100% by weight, based on the weight of said active ingredient contained in said preparation.

4. The oral sustained-release preparation according to claim 1, wherein said coating contains 0.5 to 10 parts by weight of said insoluble auxiliary material, per part by weight of said coating base material.

5. The oral sustained-release preparation according to claim 1, wherein said insoluble auxiliary material is at least one member selected from the group consisting of magnesium stearate, calcium stearate, talc, titanium oxide and light anhydrous silicic acid.

6. The oral sustained-release preparation according to claim 1, wherein said coating base material is ethylcellulose and said insoluble auxiliary material is talc.

7. An oral sustained-release preparation containing fasudil hydrochloride as an active ingredient, wherein said fasudil hydrochloride is represented by the following formula:

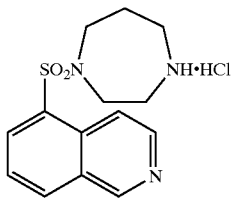

said preparation exhibiting, with respect to said active ingredient, the following dissolution rates (1), (2) and (3), as measured using a dissolution test apparatus in conformity with the Japanese Pharmacopoeia Thirteenth Edition under the conditions wherein the amount of a dissolution medium is 900 ml, the temperature of the dissolution medium is 37±0.5° C., and the revolution rate of a paddle is 100±4 revolutions per minute:
  (1) dissolution of 5 to 40% by weight, based on the weight of said active ingredient originally contained in said preparation, at the point in time of 3 hours after the start of the dissolution test,
  (2) dissolution of 35 to 70% by weight, based on the weight of said active ingredient originally contained in said preparation, at the point in time of 6 hours after the start of the dissolution test, and
  (3) dissolution of 70% by weight or more, based on the weight of said active ingredient originally contained in said preparation, at the point in time of 15 hours after the start of the dissolution test.

8. A method for evaluating an oral sustained-reiease preparation containing fasudil hydrochloride as an active ingredient, wherein said fasudil hydrochloride is represented by the following formula:

said evaluation being conducted with respect to the sustained-release ability of said preparation with respect to said fasudil hydrochloride contained therein,
said method comprising subjecting said preparation to a test according to a dissolution test method, said testing allows for selection of a preparation which maintains the concentration of an active metabolite in blood for a long period of time by conducting a standard test with a dissolution test apparatus in conformity with the Japanese Pharmacopoeia Thirteenth Edition under the conditions wherein the amount of a dissolution medium is 900 ml, the temperature of the dissolution medium is 37±0.5° C., and the revolution rate of a paddle is 100±4 revolutions per minute; and assessing a dissolution of said active ingredient from said preparation by taking as a criterion the following dissolution rates (1), (2) and (3):
  (1) dissolution of 5 to 40% by weight, based on the weight of said active ingredient originally contained in said preparation, at the point in time of 3 hours after the start of the dissolution test,
  (2) dissolution of 35 to 70% by weight, based on the weight of said active ingredient originally contained in said preparation, at the point in time of 6 hours after the start of the dissolution test, and (3) dissolution of 70% by weight or more, based on the weight of said active ingredient originally contained in said preparation, at the point in time of 15 hours after the start of the dissolution test.

9. The oral sustained-release preparation according to claim 1, wherein said core further comprises a nucleating excipient selected from the group consisting of sucrose, starch, a crystalline cellulose, or a mixture thereof.

10. The oral sustained-release preparation according to claim 1, wherein said coating base material is ethylcellulose and said insoluble auxiliary material is magnesium stearate.

11. The oral sustained-release preparation according to claim 1, wherein said coating base material is a copolymer of ethyl acrylate/methyl methacrylate/trimethylammonioethyl methacrylate chloride and said insoluble auxiliary material is talc.

* * * * *